US 9,764,043 B2

(12) United States Patent
Myerson et al.

(10) Patent No.: US 9,764,043 B2
(45) Date of Patent: Sep. 19, 2017

(54) ANTITHROMBOTIC NANOPARTICLE

(75) Inventors: Jacob Myerson, St. Louis, MO (US); Samuel A. Wickline, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 201 days.

(21) Appl. No.: 13/516,528

(22) PCT Filed: Dec. 17, 2010

(86) PCT No.: PCT/US2010/061103
§ 371 (c)(1),
(2), (4) Date: Oct. 31, 2012

(87) PCT Pub. No.: WO2011/084700
PCT Pub. Date: Jul. 14, 2011

(65) Prior Publication Data
US 2013/0064765 A1 Mar. 14, 2013

Related U.S. Application Data

(60) Provisional application No. 61/287,582, filed on Dec. 17, 2009.

(51) Int. Cl.
*A61K 47/48* (2006.01)

(52) U.S. Cl.
CPC .. *A61K 47/48807* (2013.01); *A61K 47/48053* (2013.01); *A61K 47/48215* (2013.01)

(58) Field of Classification Search
CPC ........ A61K 47/48053; A61K 47/48215; A61K 47/48807
USPC ....... 514/1, 1.1, 13.5, 13.7, 14.2, 14.7, 13.8; 424/400, 489, 1.69, 9.34, 9.5, 93.72
See application file for complete search history.

(56) References Cited

U.S. PATENT DOCUMENTS

| | | | |
|---|---|---|---|
| 3,215,572 A | 11/1965 | Papell | |
| 4,297,623 A | 10/1981 | Dupont | |
| 5,077,036 A | 12/1991 | Long | |
| 5,114,703 A | 5/1992 | Wolf | |
| 5,171,755 A | 12/1992 | Kaufman | |
| 5,260,306 A | 11/1993 | Boardman et al. | |
| 5,304,325 A | 4/1994 | Kaufman | |
| 5,350,571 A * | 9/1994 | Kaufman ............. | A61K 9/0026 424/9.37 |
| 5,393,524 A | 2/1995 | Quay | |
| 5,403,575 A | 4/1995 | Kaufman | |
| 5,534,499 A | 7/1996 | Ansell | |
| 5,690,907 A | 11/1997 | Lanza | |
| 5,780,010 A | 7/1998 | Lanza | |
| 5,820,848 A | 10/1998 | Boni et al. | |
| 5,958,371 A | 9/1999 | Lanza | |
| 5,989,520 A | 11/1999 | Lanza | |
| 6,368,586 B1 | 4/2002 | Jacob et al. | |
| 6,413,544 B1 | 7/2002 | Smyth-Templeton et al. | |
| 6,491,903 B1 | 12/2002 | Forster et al. | |
| 6,579,846 B1 | 6/2003 | Zirnstein et al. | |
| 7,022,313 B2 | 4/2006 | O'Connor et al. | |
| 9,446,150 B2 | 9/2016 | Lanza et al. | |
| 9,468,607 B2 | 10/2016 | Lanza et al. | |
| 9,498,439 B2 | 11/2016 | Lanza et al. | |
| 2002/0034536 A1 | 3/2002 | Perkins et al. | |
| 2003/0157179 A1 | 8/2003 | Blum et al. | |
| 2003/0185879 A1 | 10/2003 | Boulikas | |
| 2004/0142474 A1 | 7/2004 | Mahato et al. | |
| 2004/0229945 A1 | 11/2004 | Satchi-Fainaro et al. | |
| 2005/0037050 A1 | 2/2005 | Weber | |
| 2005/0079131 A1 | 4/2005 | Lanza et al. | |
| 2005/0095267 A1 * | 5/2005 | Campbell et al. ............ | 424/425 |
| 2006/0008461 A1 | 1/2006 | Yatvin et al. | |
| 2006/0015261 A1 * | 1/2006 | Mann et al. ..................... | 702/19 |
| 2006/0159619 A1 | 7/2006 | Becker et al. | |
| 2006/0228299 A1 | 10/2006 | Thorpe et al. | |
| 2006/0264397 A1 | 11/2006 | Kucera et al. | |
| 2007/0020308 A1 * | 1/2007 | Richard et al. ............... | 424/423 |
| 2007/0110777 A1 | 5/2007 | Joabsson et al. | |
| 2007/0154539 A1 | 7/2007 | Fountain | |
| 2008/0269875 A1 | 10/2008 | Zhao | |
| 2008/0286321 A1 | 11/2008 | Reneker et al. | |
| 2008/0286372 A1 | 11/2008 | Pacetti et al. | |
| 2009/0148383 A1 | 6/2009 | Peter | |
| 2009/0163437 A1 * | 6/2009 | Rusconi ......................... | 514/44 |
| 2009/0202429 A1 * | 8/2009 | Diacovo et al. ............. | 424/1.11 |
| 2009/0208548 A1 | 8/2009 | Mason et al. | |
| 2010/0028994 A1 | 2/2010 | DeSimone et al. | |
| 2010/0297007 A1 | 11/2010 | Lanza et al. | |
| 2010/0297019 A1 | 11/2010 | Lanza et al. | |
| 2013/0122100 A1 | 5/2013 | Lanza et al. | |
| 2016/0279060 A1 | 9/2016 | Lanza et al. | |

FOREIGN PATENT DOCUMENTS

| | | |
|---|---|---|
| WO | 96/20698 A2 | 7/1996 |
| WO | 01/74337 A1 | 10/2001 |
| WO | WO 03015831 A1 * | 2/2003 |

(Continued)

OTHER PUBLICATIONS

Di Nisio, Direct Thrombin Inhibitors, The New England Journal of Medicine, Sep. 2005, pp. 1028-40, vol. 353.
CAS Registry Record for Fumagillin (CAS # 23110-15-8). Entered STN Nov. 16, 1984, Accessed by Examiner on Mar. 3, 2016, 2 pgs.
CAS Registry Record for Fumagillol (CAS # 108102-51-8). Entered STN May 16, 1987, Accessed by Examiner on Mar. 8, 2016, 2 pgs.
Nelson, D. et al., Lehninger Principle of Biochemistry, 2000, Third Edition, Chapter 12, pp. 392-393, Worth Publishers, New York, New York.
Notice of Allowance dated Mar. 1, 2016 from related U.S. Appl. No. 12/682,098; 4 pgs.
Notice of Allowance dated Apr. 11, 2016 from related U.S. Appl. No. 13/641,252; 9 pgs.

(Continued)

*Primary Examiner* — Robert Cabral
(74) *Attorney, Agent, or Firm* — Polsinelli PC

(57) ABSTRACT

The present invention encompasses an antithrombotic nanoparticle.

13 Claims, 21 Drawing Sheets
(21 of 21 Drawing Sheet(s) Filed in Color)

(56) References Cited

FOREIGN PATENT DOCUMENTS

| | | |
|---|---|---|
| WO | 2004/017907 A2 | 3/2004 |
| WO | 2005/014051 A1 | 2/2005 |
| WO | 2006/072943 A2 | 7/2006 |
| WO | 2006/117720 A2 | 11/2006 |
| WO | 2007/034359 A2 | 3/2007 |
| WO | 2007/106683 A2 | 9/2007 |
| WO | 2008/063157 A2 | 5/2008 |
| WO | 2008/109712 A2 | 9/2008 |
| WO | 2009/049083 A1 | 4/2009 |
| WO | 2009/049089 A1 | 4/2009 |
| WO | 2009151788 A2 | 12/2009 |
| WO | 2011/084700 A1 | 7/2011 |
| WO | 2011/130674 A1 | 10/2011 |
| WO | 2011/133635 A2 | 10/2011 |
| WO | 2014/179793 A1 | 11/2014 |

OTHER PUBLICATIONS

Office Action dated Oct. 18, 2016 from related Canadian Patent Application No. 2,796,435; 3 pgs.
Office Action dated Dec. 4, 2013, from related Chinese Patent Application No. 2011800297722; 13 pgs., with English translation.
Office Action dated Nov. 9, 2016 from related European Patent Application No. 10842655.2; 8 pgs.
Office Action dated Oct. 27, 2016 from related European Patent Application No. 11769698.9; 5 pgs.
Office Action dated Jan. 12, 2017 from related U.S. Appl. No. 15/334,108; 13 pgs.
Winter et al., "Endothelial alphaVbeta3 Integrin-Targeted Fumagillin Nanoparticles Inhibit Angiogenesis in Atherosclerosis," Arterioscler. Thromb. Vasc. Biol., Sep. 2006, pp. 2103-2109, vol. 26.
Landfester et al., "Encapsulated magnetite particles for biomedical application", Journal of Physics: Condensed Matter, 2003, pp. S1345-S1361, vol. 15.
Lanza et al., "Molecular Imaging of Stretch-Induced Tissue Factor Expression in Carotid Arteries with Intravascular Ultrasound", Investigative Radiology, 2000, pp. 227-234, vol. 35, No. 4.
Lanza et al., "Targeted Antiproliferative Drug Delivery to Vascular Smooth Muscle Cells With a Magnetic Resonance maging Nanoparticle Contrast Agent: Implications for Rational Therapy of Restenosis", Circulation, 2002, pp. 2842-2847, vol. 106.
Liu et al., "Surface Modification and Characterization of Magnetic Polymer Nanospheres Prepared by Miniemulsion Polymerization", Langmuir, 2004, pp. 10278-10282, vol. 20, No. 23.
Liu et al., "Preparation and characterization of biodegradable magnetic carriers by single emulsion-solvent evaporation", Journal of Magnetism and Magnetic Materials, 2007, pp. 84-87, vol. 311.
Mandal et al., "Encapsulation of Magnetic and Fluorescent Nanoparticles in Emulsion Droplets", Langmuir, 2005, pp. 4175-4179, vol. 21, No. 9.
Montagne et al., "Preparation and characterization of narrow sized (o/w) magnetic emulsion", Journal of Magnetism and Magnetic Materials, 2002, pp. 302-312, vol. 250.
Moody et al., "Direct magnetic resonance imaging of carotid artery thrombus in acute stroke", The Lancet, 1999, pp. 122-123, vol. 353.
Morales et al., "Contrast agents for MRI based on iron oxide nanoparticles prepared by laser pyrolysis", Journal of Magnetism and Magnetic Materials, 2003, pp. 102-109, vol. 266.
Mulder et al., "MR molecular imaging and fluorescence microscopy for identification of activated tumor endothelium using a bimodal lipidic nanoparticle", The FASEB Journal, 2005, pp. 2008-2010, vol. 19.
Mulder et al., "Lipid-based nanoparticles for contrast-enhanced MRI and molecular imaging", NMR in Biomedicine, 2006, pp. 142-164, vol. 19.
Myerson et al., "'Thrombin sponge': A potent nanoparticle approach to inhibiting coagulation in acute thrombosis", The FASEB Journal, 2010, p. 574.2, vol. 24, No. 1.
Myerson et al., "Thrombin-inhibiting perfluorocarbon nanoparticles provide a novel strategy for treatment and magnetic resonance imaging of acute thrombosis", Journal of Thrombosis and Haemostasis, 2011, pp. 1292-1300, vol. 9, No. 7.
Office Action from related U.S. Appl. No. 13/641,252, dated Sep. 30, 2015; 20 pgs.
Office Action from related U.S. Appl. No. 13/641,252, dated Jun. 26, 2015; 11 pgs.
Office Action from related U.S. Appl. No. 12/682,098, dated Jun. 22, 2015; 27 pgs.
Office Action from related U.S. Appl. No. 12/682,098, dated May 9, 2013; 17 pgs.
Office Action from related U.S. Appl. No. 12/682,098, dated Jun. 11, 2012; 15 pgs.
Office Action from related U.S. Appl. No. 12/682,094, dated Jan. 14, 2013; 16 pgs.
Office Action from related U.S. Appl. No. 12/682,094, dated May 7, 2012; 15 pgs.
Office Action from related Japanese Patent Application No. 2013-505192, dated Jan. 15, 2015; 2 pgs.
First Office Action from related Chinese Patent Application No. 200880117661.5, dated Jul. 20, 2011; 11 pgs.
Second Office Action from related Chinese Patent Application No. 200880117661.5, dated Jun. 4, 2012; 17 pgs.
Third Office Action from related Chinese Patent Application No. 200880117661.5, dated Jan. 7, 2013; 13 pgs.
Fourth Office Action from related Chinese Patent Application no. 200880117661.5, dated Jul. 25, 2013; 13 pgs.
Pan, et al., "Water Soluble Nano-Bialys: Preparation of a Vascularly Constrained, Slow Releasing Nano-Carrier for Hydrophilic and Hydrophobic Drugs", Oct. 2007, Abstract for presentation in American Chemical Society, Nestern Regional Meeting 2007, Frontiers in Chemistry, Biopharmaceuticals & Biotechnology.
Pan et al., "Anti-Angiogenesis Therapy in the Vx2 Rabbit Cancer Model with Lipase-cleavable Sn 2 Taxane Phospholipid Prodrug using αvβ3-Targeted Theranostic Nanoparticles", Theranostics, 2014, pp. 565-578, vol. 4, No. 6.
Piras et al., "Polymeric nanoparticles for hemoglobin-based oxygen carriers", Biochimica et Biophysica Acta, 2008, pp. 1454-1461, vol. 1784.
Qiu et al., "Novel, Fluorescent, Magnetic, Polysaccharide-Based Microsphere for Orientation, Tracing, and Anticoagulation: Preparation and Characterization", Biomacromolecules, 2005, pp. 1041-1047, vol. 6, No. 2.
Raj et al., "Commercial Applications of Ferrofluids", Journal of Magnetism and Magnetic Materials, 1990, pp. 233-245, vol. 85.
Roath, "Biological and biomedical aspects of magnetic fluid technology", Journal of Magnetism and Magnetic Materials, 1993, pp. 329-334, vol. 122.
Roger et al., "Some biomedical applications of ferrofluids", The European Physical Journal Applied Physics, 1999, pp. 321-325, vol. 5.
Rosensweig, "Magnetic Fluids: Tiny ferromagnetic particles suspended in an organic liquid form a new kind of fluid responsive to magnetic fields in queer but useful ways", International Science and Technology, 1966, pp. 48-56.
Su, "Assembly of polydiacetylene vesicles on solid substrates", Journal of Colloid and Interface Science, 2005, pp. 271-276, vol. 292.
Thorek et al., "Superparamagnetic Iron Oxide Nanoparticle Probes for Molecular Imaging", Annals of Biomedical Engineering, 2006, pp. 23-38, vol. 34, No. 1.
Verweij et al., "Paclitaxel (Taxol) and docetaxel (Taxotere): Not simply two of a kind", Annals of Oncology, 1994, pp. 495-505, vol. 5.
Vyavahare et al., "In vitro and in vivo evaluation of the site-specific administration of D-phenylalanyl-L-prolyl-L-arginyl chloromethyl ketone (PPACK): a powerful thrombin inhibitor", Journal of Controlled Release, 1993, pp. 165-173, vol. 27, No. 2.
Winter et al., "Antiangiogenic Synergism of Integrin-Targeted Fumagillin Nanoparticles and Atorvastatin in Atherosclerosis", JACC: Cardiovascular Imaging, 2008, pp. 624-634, vol. 1, No. 5.

(56) References Cited

OTHER PUBLICATIONS

Xu et al., "Encapsulation of nanosized magnetic iron oxide by polyacrylamide via inverse miniemulsion polymerization", Journal of Magnetism and Magnetic Materials, 2004, pp. 136-143, vol. 277.
Yang et al., "Preparation of poly e-caprolactone nanoparticles containing magnetite for magnetic drug carrier", International Journal of Pharmaceutics, 2006, pp. 185-190, vol. 324, No. 2.
Zhou et al "Suppression of inflammation in a mouse model of rheumatoid arthritis using targeted lipase-labile fumagillin prodrug nanoparticles", Biomaterials, 2012, pp. 8632-8640, vol. 33.
Extended European Search Report from related European Patent Application No. EP 08 83 7973, dated Jan. 2, 2014; 9 pgs.
Extended European Search report from related European Patent Application No. EP 11769698.9, dated May 6, 2014; 3 pgs.
Extended European Search report from related European Patent Application No. EP 10 84 2655, dated May 27, 2015; 12 pgs.
Examination Report dated Dec. 10, 2015 from related Australian Application No. 2010339809. 3 pgs.
Myerson, "Thrombin-inhibiting nanoparticles rapidly constitute versatile and detectable anticlotting surfaces," Nanotechnology, Oct. 3, 2014, 29 pgs, vol. 25(39).
Connors, "Antidote for Factor Xa Anticoagulants," New England Journal of Medicine, 2015, 2 pgs., DOI: 10.1056/NEJMe1513258.
Notice of Acceptance dated Apr. 20, 2015 from related Australian Application No. 2010339809. 4 pgs.
Ambrose et al., "Angiographic Progression of Coronary Artery Disease and the Development of Myocardial Infarction", JACC, 1988, pp. 56-62, vol. 12, No. 1.
Benson, "The Present Status of Coronary Arterial Disease", Archives of Pathology & Laboratory Medicine, 1926, pp. 876-916, vol. 2.
Bibette, "Monodisperse ferrofluid emulsions", Journal of Magnetism and Magnetic Materials, 1993, pp. 37-41, vol. 122.
Bowen, "Particle Size Distribution Measurement from Millimeters to Nanometers and from Rods to Platelets", Journal of Dispersion Science and Technology, 2002, pp. 631-662, vol. 23, No. 5.
Brown et al., "Incomplete lysis of thrombus in the moderate underlying atherosclerotic lesion during intracoronary infusion of streptokinase for acute myocardial infarction: quantitative angiographic obser-vations", Circulation, 1986, pp. 653-661, vol. 73, No. 4.
Brownlie et al., "PEI-based vesicle-polymer hybrid gene delivery system with improved biocompatibility", International Journal of Pharmaceutics, 2004, pp. 41-52, vol. 274.
CASSCELLS et al., "Thermal detection of cellular infiltrates in living atherosclerotic plaques: possible implications for plaque rupture and thrombosis", The Lancet, 1996, pp. 1447-1449, vol. 347.
Cerqueira, "Current Status of Radionuclide Tracer Imaging of Thrombi and Atheroma", Seminars in Nuclear 'Medicine, 1999, pp. 339-351, vol. 29, No. 4.
Charles, "Some Applications of Magnetic Fluids—Use As an Ink and in Microwave Systems", Journal of Magnetism and Magnetic Materials, 1987, pp. 350-358, vol. 65.
Cho et al., "Ability of Surfactant Micelles to Alter the Physical Location and Reactivity of Iron in Oil-in-Water Emulsion", Journal of Agricultural and Food Chemistry, 2002, pp. 5704-5710, vol. 50, No. 20.
Constantinides, "Plaque Fissures in Human Coronary Thrombosis", Journal of Atherosclerosis Research, 1966, pp. 1-17, vol. 6.
Davies et al., "The effect of temperature and oleate adsorption on the growth of maghemite particles", Journal of Magnetism and Magnetic Materials, 1993, pp. 24-28, vol. 122.
de Korte et al., "Characterization of plaque components and vulnerability with intravascular ultrasound elastography", Phys. Med. Biol., 2000, pp. 1465-1475, vol. 45.
Deng et al., "Magnetic and conducting $Fe_3O_4$-cross-linked polyaniline nanoparticles with core-shell structure", Polymer, 2002, pp. 2179-2184, vol. 43.
Deng et al., "Preparation of magnetic polymeric particles via inverse microemulsion polymerization process", Journal of Magnetism and Magnetic Materials, 2003, pp. 69-78, vol. 257.
Dresco et al., "Preparation and Properties of Magnetite and Polymer Magnetite Nanopartides", Langmuir, 1999, pp. 1945-1951, vol. 15, No. 6.
Dubertret et al., "In Vivo Imaging of Quantum Dots Encapsulated in Phospholipid Micelles", Science, 2002, pp. 1759-1762, vol. 298.
Feltin et al., "New Technique for Synthesizing Iron Ferrite Magnetic Nanosized Particles", Langmuir, 1997, pp. 3927-3933, vol. 13, No. 15.
Forrest et al., "Partial Acetylation of Polyethylenimine Enhances in Vitro Gene Delivery", Pharmaceutical Research, 2004, pp. 365-371, vol. 21, No. 2.
Gilchrist et al., "Selective Inductive Heating of Lymph Nodes", Annals of Surgery, 1957, pp. 596-606, vol. 146, No. 4.
Glagov et al., "Compensatory Enlargement of Human Atherosclerotic Coronary Arteries", The New England Journal of Medicine, 1987, pp. 1371-1375, vol. 316, No. 22.
Hofman et al., "Quantification of In-Plane Motion of the Coronary Arteries During the Cardiac Cycle: Implications for Acquisifion Window Duration for MR Flow Quantification", Journal of Magnetic Resonance Imaging, 1998, pp. 568-576, vol. 8, No. 3.
International Search Report and Written Opinion from related International Application No. PCT/US2014/36762, dated Oct. 9, 2014; 7 pgs.
International Search Report and Written Opinion from related International Application No. PCT/US2011/32744, dated Jul. 8, 2011; 10 pgs.
International Search Report and Written Opinion from related International Application No. PCT/US2008/79404, dated Dec. 24, 2008; 8 pgs.
International Search Report and Written Opinion from related International Application No. PCT/US2008/79414, dated Dec. 15, 2008; 15 pgs.
Kim et al., "Development of a novel dosage form for intramuscular injection of titrated extract of Centella asiatica in a mixed micellar system", International Journal of Pharmaceutics, 2001, pp. 141-147, vol. 220.

* cited by examiner

A

B

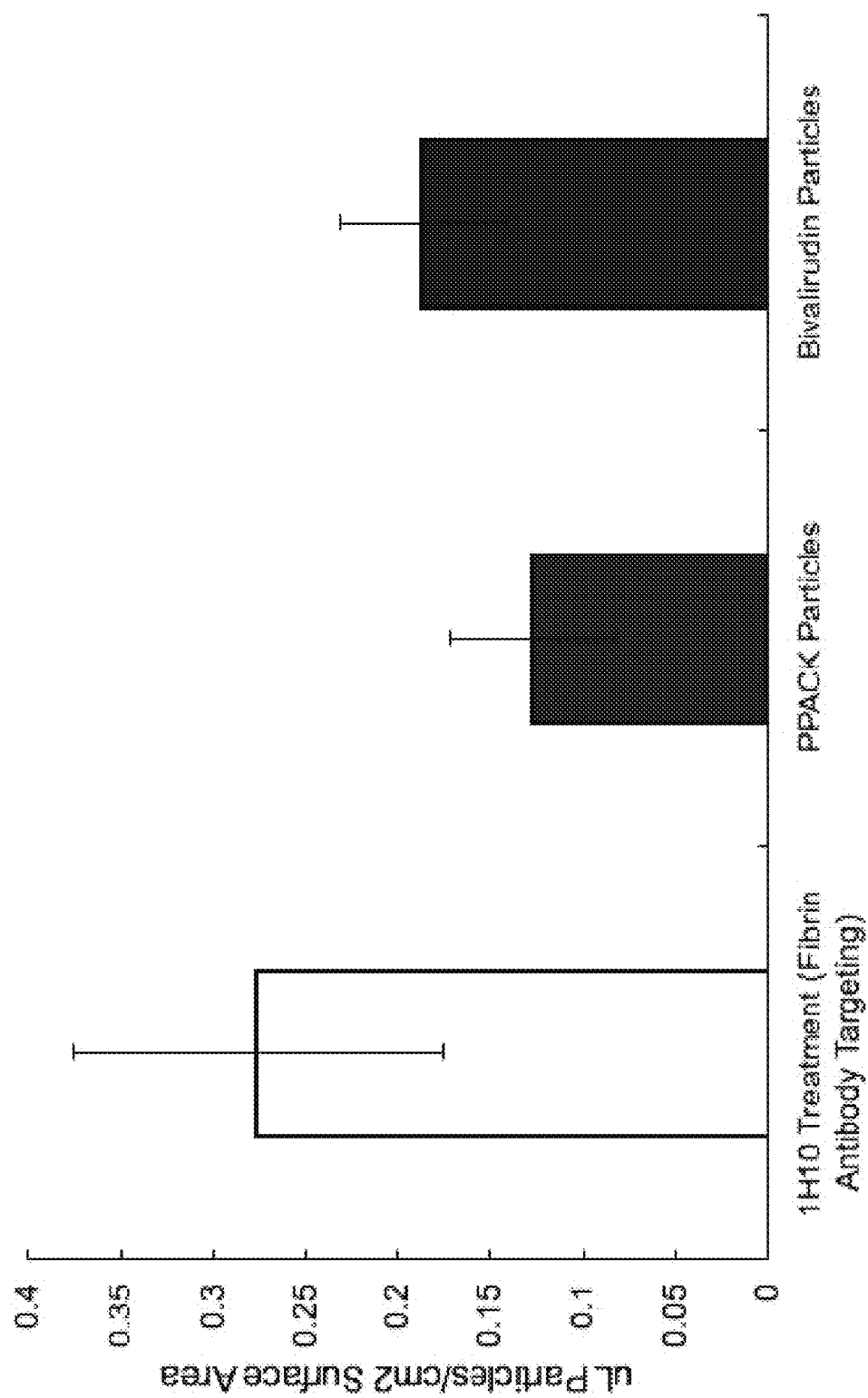

US 9,764,043 B2

ANTITHROMBOTIC NANOPARTICLE

GOVERNMENTAL RIGHTS

This invention was made with government support under grant number HL-073646 awarded by the National Institutes of Health. The government has certain rights in the invention.

FIELD OF THE INVENTION

The invention encompasses an antithrombotic nanoparticle.

BACKGROUND OF THE INVENTION

Millions of people die or are disabled each year from acute stroke or heart attack that are caused by the highly localized formation of blood clots resulting in occlusion of the carotid or coronary arteries. In cases where premonitory symptoms or signs of disease indicate the risk of an acute event, a cocktail of various anticoagulants and antiplatelet agents is administered both orally and intravenously to prevent clot progression. Even with aggressive treatment regimens, however, thrombus formation may still proceed unpredictably. Additionally, severe or fatal bleeding problems may arise with the systemically active anticoagulants in use today. Accordingly, there is a need in the art for the development of safer and more effective antithrombotics.

SUMMARY OF THE INVENTION

One aspect of the present invention encompasses an antithrombotic nanoparticle. Generally speaking, the exterior of the nanoparticle comprises at least one high affinity coagulation inhibitor that is substantially retained on the exterior of the nanoparticle after administration of the nanoparticle to a subject, such that the nanoparticle is antithrombotic but does not substantially alter the clotting time of the subject's blood plasma.

Another aspect of the present invention encompasses an antithrombotic nanoparticle. Usually the half-life of the nanoparticle is between about 2 and about 4 hours in a subject, and the exterior of the nanoparticle comprises at least one high affinity coagulation inhibitor that is substantially retained on the exterior of the nanoparticle after administration of the nanoparticle to a subject. Additionally, the second order kinetic constant of the nanoparticle is greater than the second order kinetic constant of the high affinity coagulation inhibitor by itself.

Yet another aspect of the invention encompasses a composition. The composition typically comprises a plurality of platelets, fibrin, and at least one nanoparticle, wherein the exterior of the nanoparticle comprises at least one high affinity coagulation inhibitor that is substantially retained on the exterior of the nanoparticle after in vivo administration of the nanoparticle.

Still another aspect of the invention encompasses a method of decreasing thrombus formation in a subject. The method generally comprises administering a nanoparticle to the subject. The half-life of the nanoparticle is typically between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

A further aspect of the invention encompasses a method of preventing thrombus formation in a subject. The method generally comprises administering a nanoparticle to the subject. The half-life of the nanoparticle is between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

Still a further aspect encompasses a method of imaging a thrombus in a subject. The method typically comprises administering a nanoparticle to the subject. The half-life of the nanoparticle is between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

Other aspects and iterations of the invention are described in more detail below.

BRIEF DESCRIPTION OF THE FIGURES

The application file contains at least one photograph executed in color. Copies of this patent application publication with color photographs will be provided by the Office upon request and payment of the necessary fee.

FIG. 17 depicts a graph illustrating the amount of nanoparticles per surface area of a clot. Human fibrin clots were formed via activation of citrated plasma with thrombin and 500 mM $CaCl_2$ as described previously (Morawski A M et al (2004) 52: 1255-1262.). For thrombin-targeted particles, clots were incubated with 1:15 dilution of emulsion at 37 degrees for two hours on a rotating platform shaker prior to rinsing and quantitative $^{19}$F spectroscopy. For fibrin targeting, clots were incubated with 125 ug of biotinylated 1H10 antibody at 4 degrees for 12 hours prior to incubation with avidin-functionalized nanoparticles at 37 degrees as with thrombin targeting.

DETAILED DESCRIPTION OF THE INVENTION

Figure 1A:
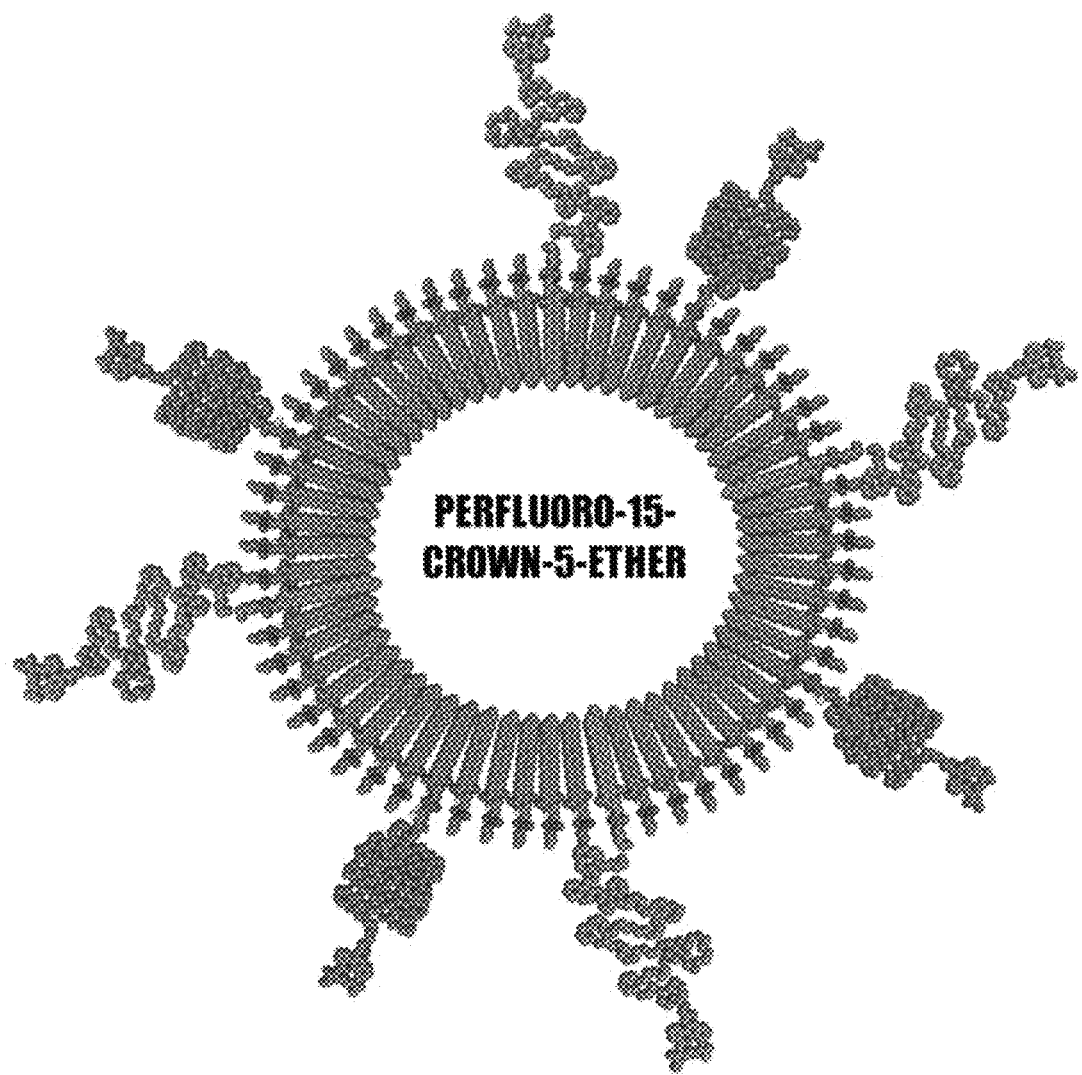
FIG. 1 depicts a schematic of the PPACK-functionalized PFC-core nanoparticle (A). The majority of the phospholipid monolayer comprised an egg lecithin L-α-phosphatidylethanolamine layer. 1% of the lipid film was 1,2-distearoyl-sn-glycero-3-phosphoethanolamine-N-[carboxy (polyethylene glycol)-2000], functionalized with PPACK after particle synthesis (B). Particle size (C) was measured before and after addition of PPACK to 1,2-distearoyl-sn-glycero-3-phosphoethanolamine-N-[carboxy(polyethylene glycol)-2000] in the lipid film. The addition of PPACK did not significantly change the mean hydrodynamic particle diameter of 158.0±2.4 nm (top panel). Corresponding to conjugation of positively charged PPACK to carboxy-terminated lipids, the particle zeta potential rose from −35±1.57 mV to −22.3±1.57 mV after functionalization (D).

The present invention provides an antithrombotic nanoparticle. Importantly, the nanoparticle is itself an integral part of the antithrombotic, as opposed to the nanoparticle simply serving as a delivery vehicle for an antithrombotic payload. The invention further provides methods of using an antithrombotic nanoparticle of the invention to prevent or decrease the formation of a thrombus in a subject.

I. Antithrombotic Nanoparticle

One aspect of the present invention encompasses an antithrombotic nanoparticle. Generally speaking, an antithrombotic nanoparticle of the invention comprises a nanoparticle structure and a high affinity coagulation inhibitor. In one embodiment, an antithrombotic nanoparticle may have anticoagulant activity. In another embodiment, an antithrombotic nanoparticle may have antiplatelet activity. In some embodiments, an antithrombotic nanoparticle may have both anticoagulant activity and antiplatelet activity. "Anti-coagulation activity," as used herein, refers to the ability to decrease fibrin based coagulation. In one embodiment, "anti-platelet activity," as used herein, refers to the ability to decrease platelet activation. In another embodiment, "anti-platelet activity" refers to the ability to decrease the density of platelets in a thrombus. In still another embodiment, "anti-platelet activity" refers to both decreasing the activation of platelets and decreasing the density of platelets in a thrombus. Methods of measuring anticoagulant and antiplatelet activity are known in the art. In one embodiment, the methods detailed in the Examples below may be used. In certain embodiments, a nanoparticle of the invention may be a PAR inhibitor.

Advantageously, a nanoparticle of the invention, while being antithrombotic at sites of active thrombus formation in a subject, does not substantially alter the clotting time of the subject's plasma. In this regard, "substantially" means that within about 20 min after intravenous administration of the nanoparticle to a subject, the subject's clotting time, as measured by an antithrombotic assay, such as an APTT assay, is about the same as the clotting time in a non-treated plasma sample.

In certain embodiments, the half-life of the antithrombotic nanoparticle after a single intravenous bolus is between about 2 hours and about 4 hours. As used herein, "half-life" refers to the elimination rate of the nanoparticle. In another embodiment, the half-life is between about 2.5 hours and about 3.5 hours. In yet another embodiment, the half-life is between about 2.75 hours and about 3.25 hours. In still another embodiment, the half-life is about 3 hours. In exemplary embodiments, a nanoparticle of the invention does not substantially alter the clotting time of the subject's plasma and has a half-life between about 2 hours and about 4 hours after a single intravenous bolus.

Generally speaking, a nanoparticle of the invention may have a more desirable kinetic constant than a high affinity coagulation inhibitor by itself. For instance, a nanoparticle of the invention comprising a high affinity coagulation inhibitor may have a greater second order kinetic constant than the second order kinetic constant of the high affinity coagulation inhibitor itself. Methods of calculating kinetic constants are known in the art. For more details, see the examples. In an exemplary embodiment, a nanoparticle of the invention does not substantially alter the clotting time of the subject's plasma, has a half-life between about 2 hours and about 4 hours, and has a greater second order kinetic constant than the high affinity inhibitor itself.

As stated above, in each of the above embodiments, a nanoparticle of the invention comprises a nanoparticle structure and a high affinity coagulation inhibitor. Each is discussed in more detail below.

(a) Nanoparticle Structure

As used herein, "nanoparticle" is used to refer to a nanostructure that is typically between about 5 nM and 400 nM across the largest dimension of the structure. A nanoparticle of the invention may be spherical, but is not required to be spherical. Regardless of the shape of the nanoparticle, the exterior of the nanoparticle should be capable of comprising at least one high affinity coagulation inhibitor.

A nanoparticle comprising an antithrombotic composition of the invention may typically be between about 5 nm and 400 nm across the largest dimension, but in some instances, may be bigger or smaller. In another embodiment, the average size of a plurality of nanoparticles in a composition may typically be between about 5 nm and 400 nm across the largest dimension. In one embodiment, the largest dimension of a nanoparticle of the invention may be between about 100 nm and about 300 nm. In another embodiment, the largest dimension of a nanoparticle may be between about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

In certain embodiments, a nanoparticle of the invention may be a perfluorocarbon nanoparticle. Such nanoparticles are known in the art. For instance, see U.S. Pat. Nos. 5,690,907; 5,780,010; 5,989,520 and 5,958,371, each hereby incorporated by reference in their entirety.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether. In some embodiments, the perfluorocarbon compound is perfluoro-n-octyl bromide. In other embodiments, the perfluorocarbon compound may be a perfluoroalkylated crown ether.

The coating which comprises lipid/surfactant to form an outer coating on the nanoparticles may include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids, including DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol, 1,2-diacyl-3-trimethylammonium-propane; 1,2-diacyl-3-dimethylammonium-propane; 1,2-diacyl-sn-glycerol-3-ethyl phosphocholine; and 3.beta.-[N',N'-dimethylaminoethane)-carbamol]cholesterol-HCl, may also be used.

Perfluorocarbon nanoparticles are typically formed by microfluidizing a mixture of the fluorocarbon lipid which forms the core and the lipid/surfactant mixture which forms the outer layer in suspension in aqueous medium to form an emulsion. Sonication or other techniques may be required to obtain a suspension of the lipid/surfactant in the aqueous medium. The components of the outer layer may also be coupled to imaging agents or radionuclides.

Other nanoparticle structures besides perfluorocarbon nanoparticles may be used in the present invention. In one embodiment, the nanoparticle structure comprises a lipid head group. For instance, a nanoparticle structure may be a liposome. Additionally, by way of non-limiting example, nanoparticles described in PCT Application numbers PCT/US2008/079404 and PCT/US2008/079414 may be used. Furthermore, in certain embodiments a colloid substance may be used as a nanoparticle of the invention. Non-limiting examples of other nanoparticle structures may include dendrimers and block di/tri copolymers. In some embodiments, cells or portions of cells may be used as the nanoparticle structure. For instance, in certain embodiments, a red blood cell or a platelet may be used as a nanoparticle structure.

(b) High Affinity Coagulation Inhibitor

Typically, the exterior of the nanoparticle comprises at least one high affinity coagulation inhibitor. As used herein, "exterior" refers to the surface of the nanoparticle that contacts blood plasma when the nanoparticle is administered to a subject. Generally speaking, the high affinity coagulation inhibitor is substantially retained on the exterior of the nanoparticle after in vivo administration of the nanoparticle to a subject. Stated another way, the high affinity coagulation inhibitor is substantially not released from the exterior of the nanoparticle after in vivo administration of the nanoparticle to a subject. A high affinity coagulation inhibitor may be attached to the nanoparticle by any means known in the art, including incorporating the high affinity coagulation inhibitor into the lipid membrane of a nanoparticle or linking the high affinity coagulation inhibitor to the nanoparticle via a linking molecule such as a peptide.

The high affinity coagulation inhibitor typically binds to a biomolecule involved in the coagulation cascade with high affinity. As used herein, "high affinity" means that the once the coagulation inhibitor binds to a biomolecule in the coagulation cascade, the biomolecule is substantially not released from the coagulation inhibitor under physiological conditions. Most high affinity coagulation inhibitors will have a Kd in the one nanomolar range, or less. In some embodiments, the high affinity coagulation inhibitor forms a covalent bond with a biomolecule involved in the coagulation cascade. In other embodiments, however, the high affinity coagulation inhibitor does not form a covalent bond with a biomolecule involved in the coagulation cascade. In some embodiments, the high affinity coagulation inhibitor inactivates the biomolecule, thereby inhibiting the coagulation cascade. In certain embodiments, the high affinity coagulation inhibitor of the antithrombotic nanoparticle binds to and sequesters the biomolecule, removing it from the coagulation cascade, thereby inhibiting the cascade. Regardless of the mechanism, the high affinity coagulation inhibitor impedes the formation of a new thrombus or impedes growth of an existing thrombus.

An antithrombotic nanoparticle may comprise one or more than one different type of high affinity coagulation inhibitor. For instance, a nanoparticle may comprise one, two, three, four, five, six, seven, or more than seven different types of high affinity coagulation inhibitor. Generally speaking, irrespective of the number of different types of high affinity coagulation inhibitors, a nanoparticle of the invention typically comprises between 3,000 and 20,000 copies of a high affinity inhibitor in total. In one embodiment, an antithrombotic nanoparticle comprises between about 5,000 and about 18,000 copies of a high affinity inhibitor. In another embodiment, a nanoparticle may comprise between about 8,000 and about 15,000 copies of a high affinity inhibitor. In still another embodiment, a nanoparticle may comprise between about 10,000 copies and about 15,000 copies of a high affinity inhibitor. In some embodiments, a nanoparticle may comprise about 10,000, about 10,500, about 11,000, about 11,500, about 12,000, about 12,500, about 13,000, about 13,500, about 14,000, about 14,500, or about 15,000 copies of a high affinity inhibitor.

As stated above, a high affinity coagulation inhibitor may bind to a biomolecule involved in the coagulation cascade such that the coagulation cascade is inhibited. In some embodiments, the high affinity coagulation inhibitor binds to thrombin. A high affinity coagulation inhibitor that bind to thrombin may be a naturally occurring inhibitor, an irreversible inhibitor, a reversible covalent inhibitor, or a reversible non-covalent inhibitor. A non-limiting example of a high affinity naturally occurring inhibitor is Hirudin ($IC_{50}$ 0.3 pM). A non-limiting example of a reversible inhibitor is Bivalirudin. A non-limiting example of an irreversible inhibitor is PPACK, which interacts with thrombin by alkylation or acylation of the active site histidine and/or formation of an acyl enzyme complex through reaction with the active site serine. Generally speaking, reversible covalent thrombin inhibitors bind to the catalytic serine hydroxyl (e.g. Efegatran $K_i$ 1.2 nM). Non-limiting examples of reversible non-covalent inhibitors may include inhibitors derived from N-a-tosylarginine methyl ester (e.g. Argatroban $K_i$ 19 nM), tripeptide inhibitors (e.g. Inogatran $K_i$ 15 nM), pyridinone/pyrazinone acetamide inhibitors (e.g. L-375,378 $K_i$ 0.8 nM), benzene/benzothiophene substitution derived inhibitors (e.g. L-636,619 $K_i$ 0.7 µM), and conformationally strained inhibitors (e.g. conformationally strained bicyclic pyridones $K_i$~2 nM). In an exemplary embodiment, the high affinity coagulation inhibitor is PPACK. In another exemplary embodiment, a nanoparticle comprises PPACK with at least one other high affinity coagulation inhibitor. In still another exemplary embodiment, a nanoparticle comprises PPACK and Bivalirudin.

In other embodiments, the high affinity coagulation inhibitor binds to a molecule listed in Table A.

TABLE A

I (fibrinogen)
II (prothrombin)
Tissue factor
V (proaccelerin, labile factor)
VII (stable factor)
VIII (Anti Hemophilic factor A)
IX (Anti Hemophilic Factor B or Christmas factor)
X (Stuart-Prower factor)
XI (plasma thromboplastin antecedent)
XII (Hageman factor)
XIII (fibrin-stabilizing factor)
von Willebrand factor
prekallikrein
high-molecular-weight kininogen (HMWK)
fibronectin A high affinity coagulation inhibitor may be incorporated into the exterior of the nanoparticle using any method known in the art, so long as the high affinity inhibitor is substantially retained on the exterior of the nanoparticle and is substantially active once incorporated into the exterior of the nanoparticle. In this regard, "substantially active" refers to the high affinity coagulation inhibitor having at least about 85, 86, 87, 88, 89, 90, 91, 92, 93, 94, 95, 96, 97, 98, 99, or 100% of its activity once incorporated into the exterior of the nanoparticle. In one embodiment, a high affinity coagulation inhibitor may be incorporated as described in the Examples below. In another embodiment, a high affinity coagulation inhibitor may be incorporated into the exterior of a nanoparticle using linkers as described in PCT/US2009/041000.

In some embodiments, a nanoparticle of the invention may comprise a high affinity coagulation inhibitor that, by itself, has an undesirable safety profile for in vivo use. This is due, in part, because the pharmacokinetic and pharmacodynamic properties of the nanoparticle may be different than the properties of the high affinity coagulation inhibitor by itself.

(c) Imaging Agent

A nanoparticle of the invention may also comprise an imaging agent. For instance, the nanoparticle maycomprise imaging/tracking agents that may be used for microscopy, e.g. fluorescent microscopy, confocal microscopy, or electron microscopy, magnetic resonance imaging, tomography, such as gamma (SPECT/CT, planar) and positron emission tomography (PET/CT), radiography, or ultrasound. Imaging/tracking agents may be detectable in situ, in vivo, ex vivo, and in vitro. Microscopy imaging/tracking agents are well known in the art, and may include fluorescent molecules such as FITC, rhodamine, and Alexafluor cyan dyes. Similarly, magnetic resonance imaging molecules, radiography imaging molecules, near infrared (NIR) and photoacoustic molecules are well known in the art, and an appropriate imaging molecule may be selected by one of skill in the art after consideration of the composition of the particle and the intended use of the particle. In certain embodiments, the nanoparticle may also comprise chelators for radiometals to be detected by nuclear imaging methods, such as PET, SPECT, and related methodologies.

(d) Other Components

A nanoparticle of the invention may further comprise other components, such as one or more anti-platelet agents, glycoprotein inhibitors, fibrinolytic agents, thrombolytic agents, antibodies, or small molecule drugs. Non-limiting examples may include streptokinase, urokinase, or tissue plasminogen.

II. Methods

A nanoparticle of the invention may be administered to a subject to prevent and/or decrease the formation of a thrombus in a subject. In one embodiment, a nanoparticle of the invention may be administered to a subject to prevent formation of a thrombus in a subject. In another embodiment, a nanoparticle of the invention may be administered to a subject to decrease the formation of a thrombus in a subject. In yet another embodiment, a nanoparticle of the invention may be used to increase the time needed for a clot to occlude a vessel.

A nanoparticle of the invention may be administered to a subject to prevent and/or decrease formation of a thrombus in both acute and non-acute situations. For instance, by way of non-limiting example, an antithrombotic nanoparticle may be administered to a subject in the acute situations of ischemia and deep vein thrombosis. Alternatively, a nanoparticle may be administered to a subject in the following non-limiting non-acute situations of stents, angioplasty, indwelling lines, artificial heart valves, shunts, or other prosthetic items in the vascular system.

In each of the above embodiments, a nanoparticle is administered to a subject. Generally speaking, a nanoparticle of the invention may be administered intravenously. A nanoparticle may also be administered orally, intramuscularly, intradermally, intraperitoneally, intralymphaticly, percutaneously, or by scarification, subcutaneous injection or other parenteral routes.

In each of the above embodiments, a nanoparticle of the invention maybe combined with a pharmaceutically acceptable vehicle or carrier. For instance, in embodiments where these compositions are administration by injection (e.g., intraperitoneally, intravenously, subcutaneously, intramuscularly, etc.), the compositions are preferably combined with pharmaceutically acceptable vehicles such as saline, Ringer's solution, dextrose solution, and the like.

One of skill in the art will recognize that the amount of a nanoparticle administered to a subject can and will vary depending on several factors, such as the size of the subject, the health of the subject, the intended use of the nanoparticle and/or the type of nanoparticle. In one embodiment, the amount of nanoparticle administered is between about 0.25 µmol/kg and about 3 µmol/kg. In another embodiment, the amount of nanoparticle administered is between about 0.5 µmol/kg and about 1.5 µmol/kg. In yet another embodiment, the amount of nanoparticle administered is about 1 µmol/kg. In still another embodiment, the amount of nanoparticle administered is between about 0.3 g/kg and about 0.4 g/kg.

Generally speaking, a nanoparticle of the invention may be administered to a subject as frequently as necessary to prevent and/or decrease the formation of a thrombus in the subject. In one embodiment, a nanoparticle may be administered every hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, or every 24 hours. In another embodiment, a nanoparticle may be administered once daily. In yet another embodiment, a nanoparticle may be administered every two days, every three days, every four days, every five days, every six days, or every seven days.

Suitable subjects may include rodents, companion animals, livestock animals, non-human primates, and humans. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of non-human primates may include capuchin monkeys, chimpanzees, lemurs, macaques, marmosets, tamarins, spider monkeys, squirrel monkeys, and vervet monkeys.

In each of the above embodiments, a nanoparticle of the invention may also be used to image a thrombus comprising one or more nanoparticles of the invention. In particular, a nanoparticle of the invention may comprise an imaging agent, such that the particle may be detected by fluorescent microscopy, confocal microscopy, or electron microscopy, magnetic resonance imaging, tomography, such as gamma (SPECT/CT, planar) and positron emission tomography (PET/CT), radiography, or ultrasound.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Introduction for Examples 1-3

In cases of cardiovascular disease, the most prevalent and costly medical emergencies faced by many millions of patients each year are the acute onset of localized thrombosis in the coronary and carotid arteries that lead to heart attack and stroke. Even with aggressive treatment with various anticoagulants and antiplatelet agents [1-5], thrombus formation can proceed unpredictably [6, 7]. Conversely, severe bleeding problems can arise using the current array of systemically active anticoagulants [8]. Furthermore, stuttering thrombosis and microembolization can effect the assessment of outcomes with current treatment strategies [9]. The development of safer and more effective anticoagulants and the tracking of clotting remain as challenges and active pursuits in research of the thrombosis-prone conditions that lead to heart attack and stroke [1, 3, 5, 10-14].

The serine protease thrombin has a central role as a rate-limiting factor in clotting. In its primary procoagulant role, thrombin converts soluble fibrinogen into insoluble fibrin that accumulates in forming clots [4, 15, and 16]. Additionally, it contributes to the activation of platelets via cleavage of G protein-coupled protease-activated receptors (PARs) [4, 15, 17-21] and plays a role upstream in the coagulation cascade through activation of factors V, VIII, and XI [22]. Elevated levels of active thrombin persist around sites of vascular injury [23]. In atherosclerosis, thrombin is associated with plaque development and susceptibility to rupture [17, 24, and 25].

Accordingly, thrombin inhibition has long been a target for development of new anticoagulants. In particular, direct thrombin inhibitors have been designed for acute treatment with high specificity and potency [2-4]. D-phenylalyl-L-prolyl-L-arginyl-chloromethyl ketone (PPACK) is an irreversible covalent inhibitor that was amongst the first direct thrombin inhibitors. The PPACK-thrombin complex has been thoroughly characterized as a stable structure [2, 4, 15, 16, and 26]. Additionally, the molecule has an excellent safety profile in vivo, with an $LD_{50}$ greater than 50 mg/kg and no long-term toxicity in mice [2, 27]. Nonetheless, therapeutic use of PPACK has been abandoned primarily due to its rapid clearance (7 minute distribution and 2.9 minute elimination half lives).

Reported herein a perfluorocarbon (PFC) nanoparticle-based antithrombotic agent and its superiority in vivo to conventional systemic anticoagulants is demonstrated in a realistic thrombosis model. The promise of the described particle is twofold. First, it enables researchers to revisit the use of potent inhibitors such as PPACK that may have been dismissed in consideration of pharmacokinetics or pharmacodynamics. Each particle permanently carries on its surface more than 10,000 covalently conjugated PPACK molecules. Whereas PPACK itself is quickly eliminated from the blood, the PFC nanoparticle has well-established pharmacokinetics (~3 hour elimination half-life) enabling a prolonged therapeutic effect that proved to be more potent than that provided by PPACK itself [28, 29]. Secondly, the particle specifically binds at the site of thrombosis, focusing the impact of the particle at the site of injury and minimizing systemic effects. Through thrombin-specific binding and the magnetic resonance contrast provided by the particle core, particles functionalized with anti-thrombins allow visualization of a thrombotic occlusion in 19F MRI. While nanoparticles have previously been employed to carry common anticoagulants [30], none have been conceptualized or demonstrated in vivo as integrated antithrombotics where the nanoparticle itself plays a critical role in diagnosis and treatment of thrombosis. [10, 26].

Materials and Methods for Examples 1-3

Nanoparticle Synthesis

Perfluorocarbon nanoparticles were prepared as described in previous work [36]. The emulsions contained 20% (vol/vol) Perfluoro 15-Crown-5 Ether (Exfluor Research Corp.), 2% (wt/vol) of a surfactant mixture, 1.7% (wt/vol) glycerin, and water for the balance. The surfactant, including 98.5 mole % phosphatidylethanolamine (Avanti Polar Lipids) and 1.5 mole % 1,2-distearoyl-sn-glycero-3-phosphoethanolamine-N-[carboxy(polyethylene glycol)-2000] (Avanti Polar Lipids) or 98 mole % egg yolk phosphotidylcholine (Avanti Polar Lipids) and 2 mole % phosphatidylethanolamine (Avanti Polar Lipids) in chloroform:methanol (3:1), was dried under vacuum to form a lipid film. The surfactant components were combined with the crown ether and distilled de-ionized water and emulsified (Microfluidics Inc) at 20000 psi for 4 minutes. Particle sizes were measured immediately after synthesis using a laser light scattering submicron particle analyzer (Brookhaven Instruments).

To functionalize particles containing 1,2-distearoyl-sn-glycero-3-phosphoethanolamine-N-[carboxy(polyethylene glycol)-2000] with PPACK, amine-carboxyl coupling was employed to conjugate the PPACK N-terminus to the bare carboxyl groups on the synthesized particles. After one hour mixing of 1 mL emulsion with 12.5 mg PPACK, EDCI 1-[3-(Dimethylamino)propyl]-3-ethylcarbodiimide methiodide (2 mg) was added for overnight coupling. Excess PPACK and EDCI were removed by dialysis (MWCO 3000-5000). Particle size was assessed before and after PPACK conjugation as described above. Extent of PPACK coupling was determined by reverse-phase HPLC quantification of uncoupled PPACK after centrifugation of nanoparticles with Cleanascite lipid adsorption reagent (Agilent Technologies). Elution of PPACK at 22 minutes after injection in a $C_{18}$ column was achieved with an isocratic method employing 9.9% acetonitrile, 0.089% trifluoroacetic acid, and 90.011% water flowed at 1 mL/minute. PPACK was detected via phenylalanine absorbance (258 nm). Zeta potential measurements, taking into consideration hydrodynamic diameter measurements, were used for further verification of PPACK coupling (Brookhaven Instruments).

Thrombin Inhibition Experiments

Tosyl-Gly-Pro-Arg-4 nitranilide acetate (Chromozym TH, Roche Applied Science) was employed to assay PPACK inhibition of thrombin and plasmin in accordance with previously described methods [31]. 100 µL of 12 nM thrombin was incubated for one minute at room temperature with selected amounts of PPACK or PPACK-nanoparticles or with an excess of bare nanoparticles. 500 µL (100 µM) of the thrombin substrate Tosyl-Gly-Pro-Arg-4 nitranilide acetate were added to terminate the PPACK-thrombin interaction. In accordance with previous work, thrombin activity against the substrate was measured via absorbance at 405 nm. The rate of change in absorbance at 405 nm was taken as representative of the amount of uninhibited thrombin available to cleave Chromozym TH.

In additional experiments, Chromozym TH was used to determine the kinetics of the PPACK-thrombin interaction. 0.92 nM thrombin was incubated at room temperature with 5 nM PPACK or 0.3 pM PPACK nanoparticles over various times prior to introduction of 500 µL of 100 µM Chromozym TH. Thrombin activity was measured as above. Kinetics of inhibition were characterized in accordance with the work of Kettner and Shaw [26]. The assay yielded the apparent pseudo-first-order rate constant for thrombin inactivation ($k_{app}$). Modeling inhibition according to equation (1), an estimate of the second order constants ($k_2/K_i$) for the PPACK-thrombin interaction and the PPACK nanoparticle-thrombin interaction were obtained via equation (2). To best obtain a pseudo-first-order reaction, thrombin dilution was maximized within the limits set by the sensitivity of the Chromozym TH assay.

$$\frac{k_{app}}{[PPACK]} = \frac{k2}{K_i} \text{ if } [PPACK] << K_i \quad (2)$$

Chromozym TH was also used to measure PPACK and PPACK nanoparticle activity against plasmin. 120 nM Plasmin was incubated for three minutes at room temperature with selected quantities of PPACK and PPACK nanoparticles. 1000-fold excess (138 μM) of PPACK (free or on nanoparticles) was employed to produce a measurable effect on plasmin activity against Chromozym TH. Activity after incubation with PPACK and PPACK nanoparticles was compared.

Antithrombotic Effects In Vivo

As described in previous work [31,32], 10-12 week old male C57BL/6 mice (weight 25-30 g) were subjected to photochemical injury of the carotid. After anesthetization with sodium pentobarbital, the mice were secured under a dissecting microscope for isolation of the right common carotid artery via midline cervical incision. An ultrasonic flow probe (model 0.5 VB Transonic Systems, Ithaca, N.Y.) was applied to the artery to measure flow for the duration of each experiment. A 1.5 mW 540 nm HeNe laser (Melles Griot, Carlsbad, Calif.) was focused on the artery at a distance of 6 cm. Heparin (0.125 mg/kg, n=4), PPACK (12.5 mg/kg, n=7), PPACK nanoparticles (1 mL/kg, n=7), or non-functionalized nanoparticles (1 mL/kg, n=7) were administered to the tail vein as a bolus 10 minutes prior to inducing arterial thrombus through tail vein injection of photosensitive rose bengal dye (50 mg/kg; Fisher Scientific, Fair Lawn, N.J.) dissolved in PBS. In additional control experiments (n=4), no treatment preceded injection of the rose bengal dye. Occlusion of the carotid artery was noted and experiments were terminated upon the stable (>5 minutes) maintenance of zero flow.

Occluded arteries were removed and preserved. For transmission electron microscopy, arteries were fixed in 2% glutaraldehyde and 0.1 mM sodium cacodylate at 4 degrees. Fixed tissues were stained with osmium tetroxide, tannic acid, and uranyl acetate. Tissues were then dehydrated and embedded in PolyBed 812 (Polysciences). Semi-thin sections were stained with Toluidine Blue and evaluated under light microscope for the presence of occlusive clotting. Portions of arteries identified as containing thrombi were subsequently sliced for transmission electron microscopy. Thin sections were counterstained with uranyl acetate and lead citrate. Samples were examined with a Zeiss 902 Electron Microscope and images were recorded with Kodak EM film.

For Carstair's staining, arteries were preserved in 10% buffered formalin for 3 days. After processing through alcohols and xylenes, the arteries were embedded in paraffin and sectioned at 5-micron thickness. Hydrated sections were treated with 5% ferric alum, Mayer's hematoxylin, picric acid-orange G solution, poncean-fuchsin solution, 1% phosphotungstic acid, and aniline blue to stain for fibrin, platelets, collagen, muscle, and red blood cells. Images were analyzed for platelet content using ImageJ.

In additional mice, APTTs for blood obtained via left-ventricular draws were used to determine the systemic effects of the particles. Citrate-anticoagulated blood was obtained 10, 20, 40, 70, 110, or 150 minutes after injection of a bolus of PPACK nanoparticles or 10 minutes after injection of control nanoparticles or saline. Plasma was combined with APTT reagent (Beckman-Coulter/Instrumentation Laboratory) for three minutes prior to activation with calcium chloride and mechanical determination of coagulation time.

Imaging and Quantification of Nanoparticle Antithrombotics

Left (unaffected) and right (injured) arteries from six mice were reserved for analysis via magnetic resonance imaging and spectroscopy. Three of these mice received PPACK nanoparticles and three received blank nanoparticles prior to induction of thrombosis. Arteries were excised and rinsed with saline to remove retained blood prior to submersion in fixative as described above. Imaging and spectroscopy was conducted with a custom-built single-turn solenoid coil on a Varian 11.7T MR system. $^{19}F$ signal from nanoparticles in the artery and from a perfluorooctylbromide standard was assessed via spin echo spectroscopy (3 s pulse repetition time (TR), 2 ms echo time (TE), 256 signal averages (NT), 13.25 minute acquisition time). $^{19}F$ spin echo images (1.3 s TR, 12 ms TE, 512 signal averages, 32 phase encoding steps, 64 frequency encoding steps, 9 mm×6 mm×1 mm field of view) were obtained to depict nanoparticle binding in the excised artery. 1H spin echo images (1.5 s TR, 20 ms TE, 4 signal averages, 128 phase encoding steps, 256 frequency encoding steps, 9 mm×6 mm×1 mm field of view, 5 0.2 mm slices) allowed coregistration of the fluorine images with an anatomical image of the artery.

Example 1. Nanoparticle Synthesis

Figure 1B:
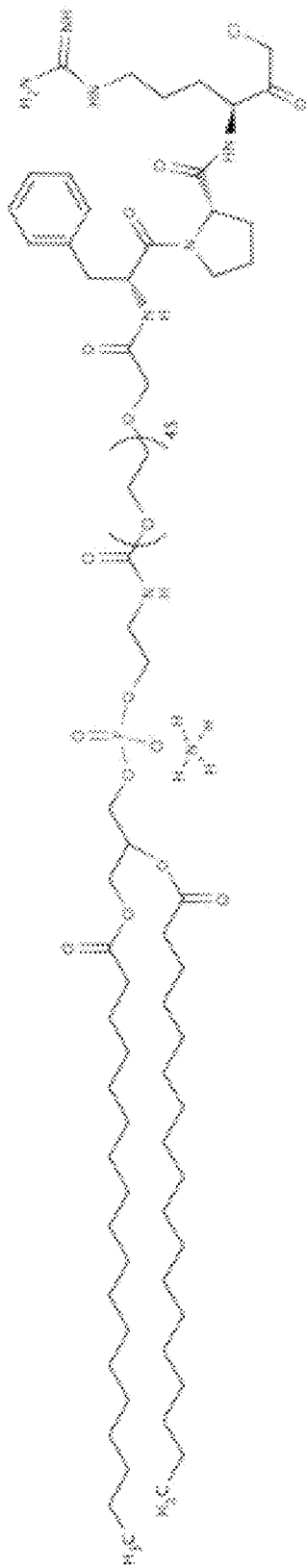
Figure 1C:
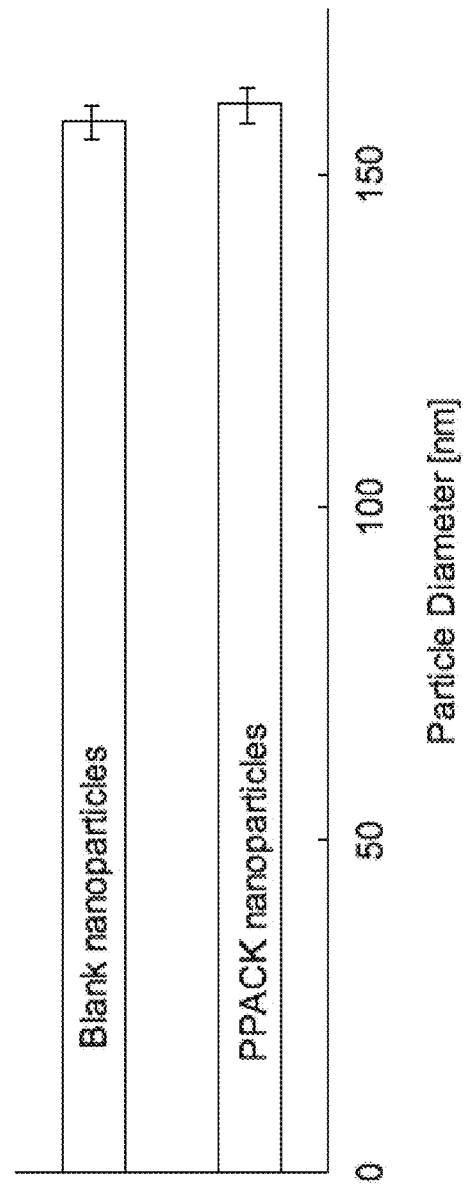

PFC nanoparticles were synthesized with inclusion of carboxy-terminated PEG capped lipids (FIGS. 1A, 1B). Via EDCI coupling, amide bonds were formed between the N-terminus of PPACK and the bare carboxyls on the particle surface. After conjugation of PPACK, nanoparticles were examined to verify stability. Precursor nanoparticles were found via laser scattering to have a hydrodynamic diameter of 158.0±2.4 nm. PPACK nanoparticles had a measured diameter of 160.5 0±2.6 nm (FIG. 1C).

Figure 1D:
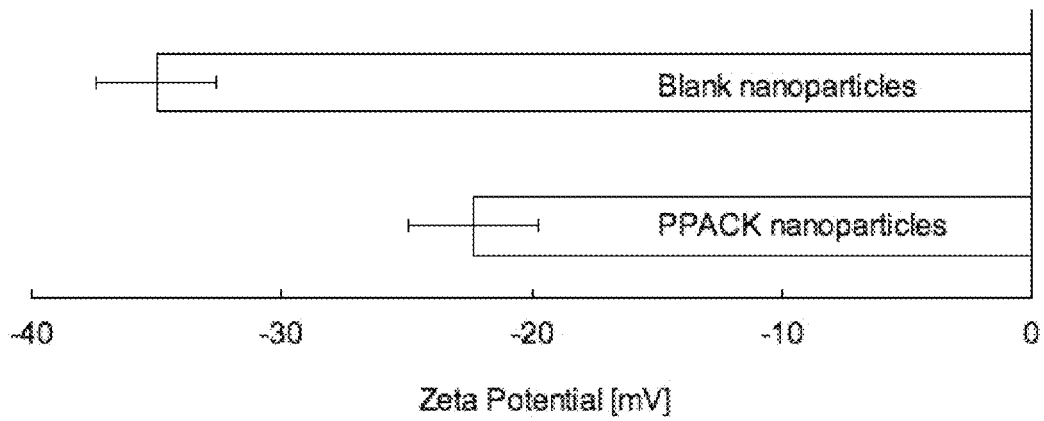

After PPACK coupling, a change in the composition of the lipid surface of the particles was evident via measurement of zeta potential. Prior to PPACK coupling, the particles exhibited a zeta potential of −35.0±1.57 mV. After addition of PPACK, the zeta potential rose to −22.3±1.57 mV, concordant with the expectation that the PPACK arginine would reduce the negative zeta potential of the non-functionalized nanoemulsions (FIG. 1D).

Figure 2:
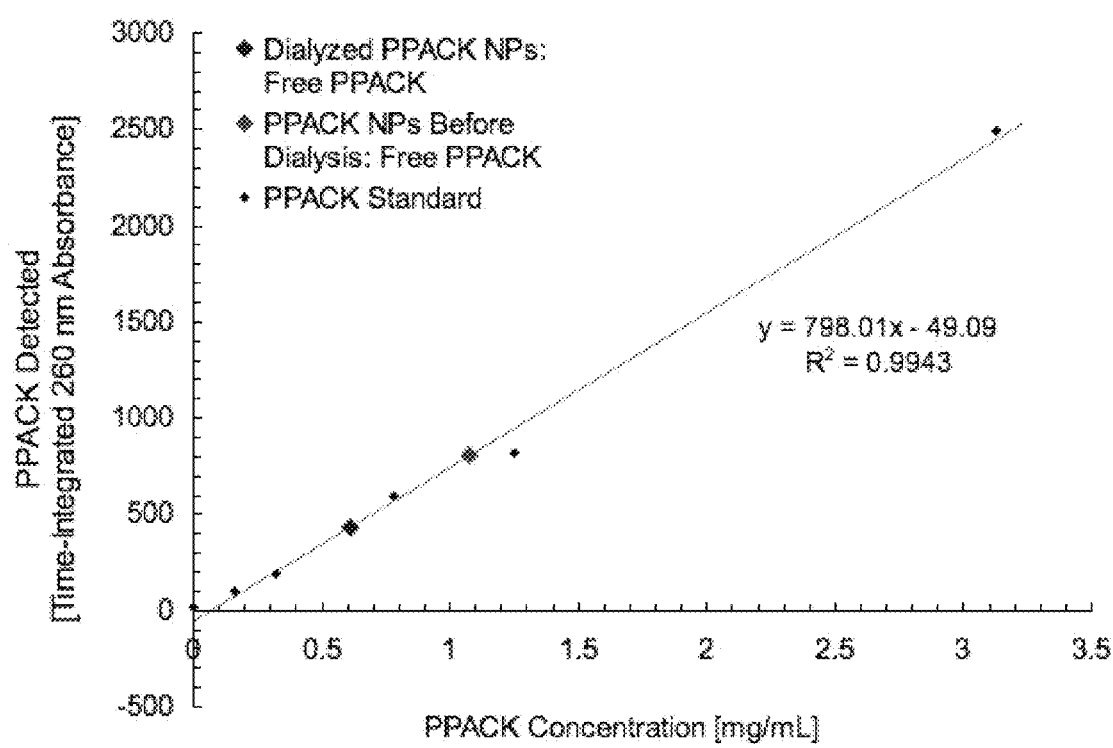
FIG. 2 depicts a graph illustrating PPACK loading on nanoparticles. Addition of ~13650 PPACK per particle was verified through HPLC quantification. The PPACK elution time for the chosen method was identified in seven samples of pure PPACK of different concentrations to generate a standard curve. Immediately after coupling of PPACK to the particles, the particles were precipitated and PPACK in the supernatant was quantified through the same method (red). Free PPACK and EDCI coupling agent were removed by dialysis and the isolated particles were precipitated identically after one week storage at 4 degrees, allowing quantification of PPACK still remaining unattached to the particles (blue).

Following synthesis but before dialysis to remove PPACK that did not couple to the particles, the residual uncoupled PPACK in the emulsion was quantified by reverse phase liquid chromatography. For PPACK nanoparticles not subject to dialysis, HPLC analysis indicated approximately 13650 PPACK coupled to each particle. HPLC also determined the amount of PPACK not associated with the particles after dialysis and one week storage at four degrees, indicating good stability of the PPACK nanoparticle formulation (FIG. 2).

Example 2. Kinetics and Specificity of Thrombin Inhibition

Figure 3A:
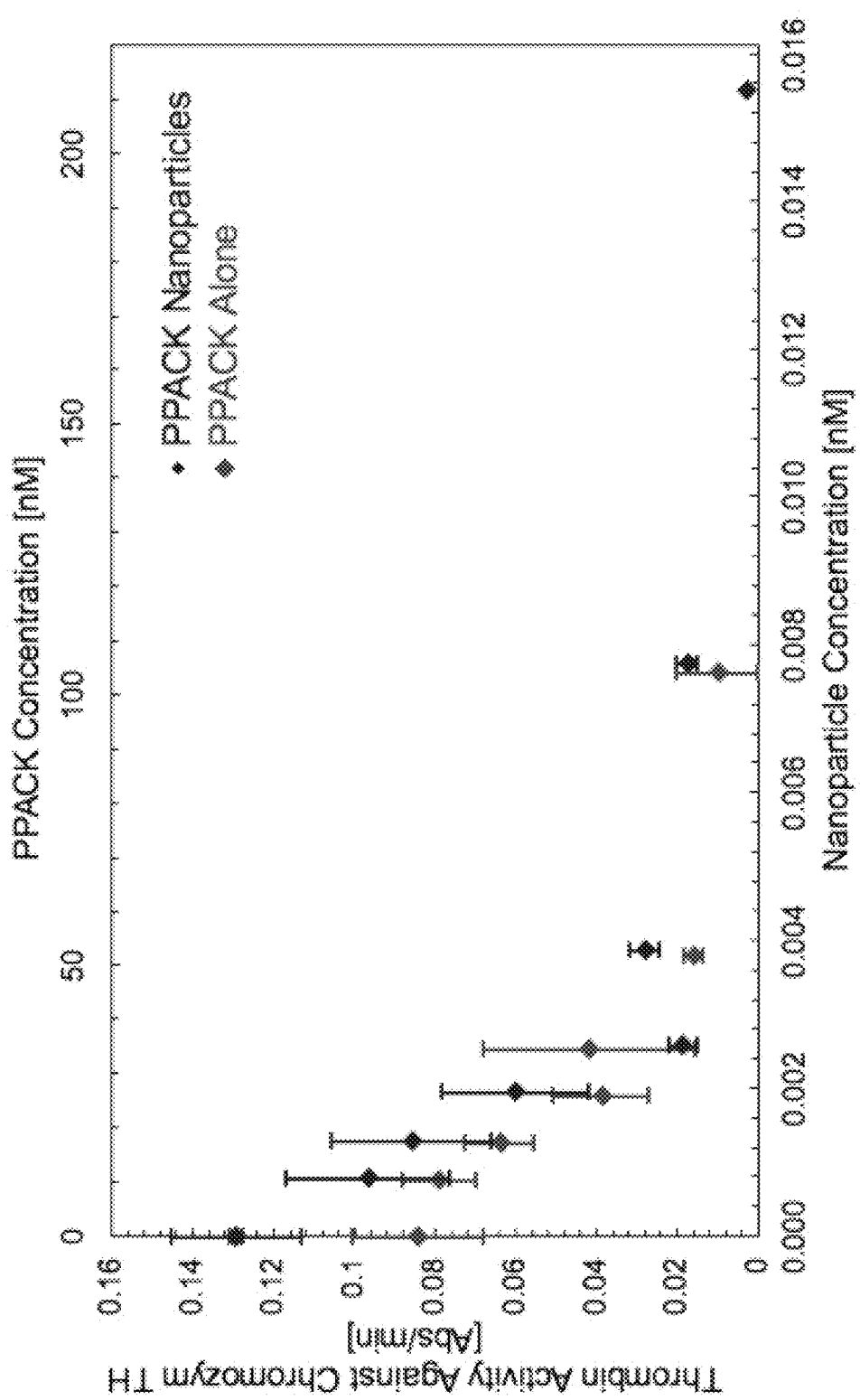
FIG. 3 depicts graphs illustrating the activity of the antithrombotic nanoparticle. PPACK caused concentration-dependent inhibition of thrombin activity against Chromozym TH, with no significant thrombin activity apparent beyond a ten-fold excess of PPACK. For PPACK-nanoparticles, the dependence of thrombin activity on PPACK concentration was identical to that for free PPACK, accordingly indicating greater antithrombin activity per particle than per individual free PPACK (A). Study of the kinetics of thrombin-PPACK and the thrombin-PPACK nanoparticle interactions indicated no modification to PPACK activity against thrombin after placement on nanoparticles (b). For 0.93 nM thrombin and 5 nM PPACK (0.0003 nM PPACK-nanoparticles), PPACK exhibited a second order constant ($k_2/K_I$) of $3.65 \times 10^8$ M$^{-1}$ min$^{-1}$ and PPACK-nanoparticles exhibited a second order constant of $6.10 \times 10^{12}$ M$^{-1}$ min$^{-1}$ (corresponding to $4.47 \times 10^8$ M$^{-1}$ min$^{-1}$ for PPACK on the particles).

PPACK and PPACK nanoparticle inhibition of thrombin was evaluated by measuring thrombin activity on the chromogenic substrate, Chromozym TH. After one-minute incubation with either PPACK nanoparticles or free PPACK, thrombin activity against the substrate decreased monotonically with increasing inhibitor concentration (FIG. 3A). PPACK on the nanoparticles gave a decay constant of 0.033 $nM^{-1}$ and free PPACK gave a decay constant of 0.026 $nM^{-1}$, indicating no diminution of PPACK activity after conjugation to particles. Complete inhibition of thrombin activity was achieved at a 15.5 pM particle concentration, corresponding to deactivation of approximately 1000 thrombin by each particle.

Figure 3B:
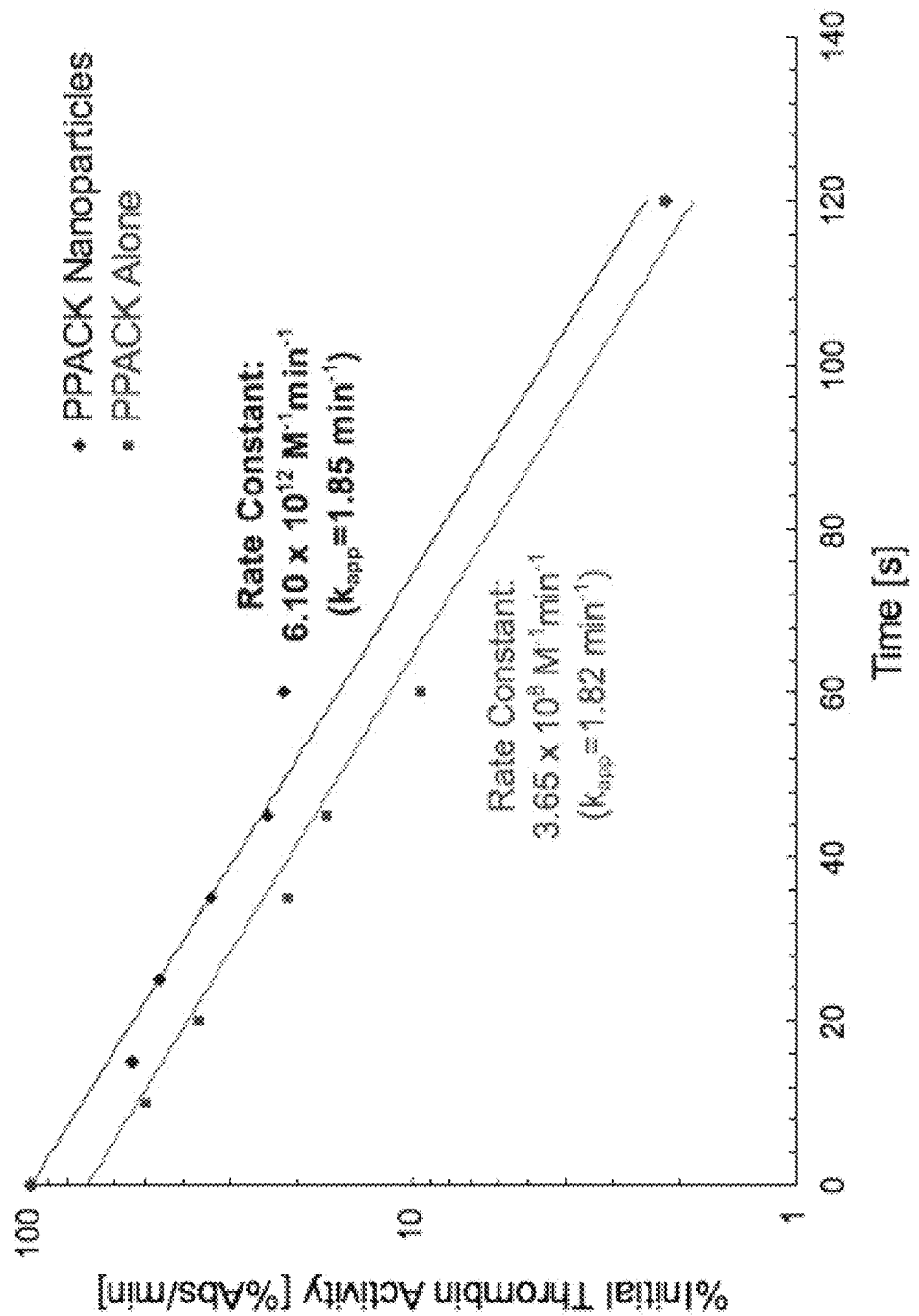

Chromozym TH assay also defined the kinetics of PPACK and PPACK nanoparticle inhibition of thrombin in accordance with the model of Kettner and Shaw (FIG. 3B). For free PPACK, the pseudo-first-order rate constant, $k_{app}$, was measured as 1.824 $min^{-1}$. The second order constant for free PPACK was approximated as $k_{app}$/[PPACK]=$3.65 \times 10^8$ $M^{-1}$ $min^{-1}$ (whereas Kettner and Shaw originally found a constant of $1.20 \times 10^9$ $M^{-1}$ $min^{-1}$ [26]). PPACK on the nanoparticles exhibited a $k_{app}$ of 1.848 $min^{-1}$ and a second order constant of $4.47 \times 10^8$ $M^{-1}$ $min^{-1}$. The PPACK nanoparticle, considered as an inhibitor itself, exhibited a second order constant of $6.10 \times 10^{12}$ $M^{-1}$ $min^{-1}$. PPACK nanoparticles at the site of thrombotic injury thus have a kinetic advantage over free PPACK in the inhibition of thrombus formation. Furthermore, the kinetics of the PPACK-thrombin interaction showed no significant alteration with PPACK bound to nanoparticles. Without PPACK, the nanoparticles had no effect on thrombin activity.

Figure 4:
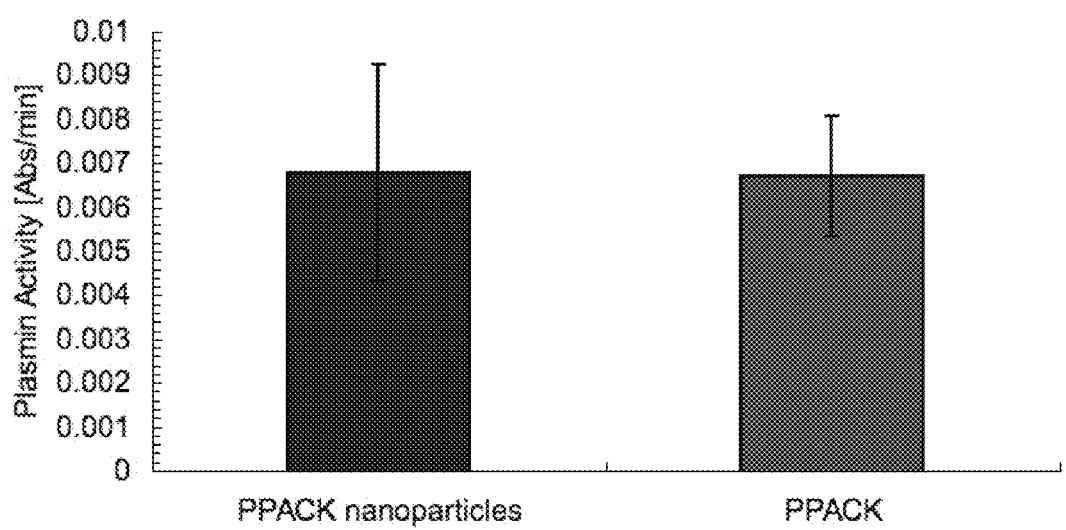
FIG. 4 depicts graphs of PPACK and PPACK-nanoparticle activity against plasmin when tested via assessment of plasmin activity against Chromozym TH. A 1000-fold excess of PPACK generated 85% suppression of plasmin activity (red). Conjugation of PPACK to nanoparticles (blue) generated no additional non-specific activity against plasmin.

Chromozym TH was used to test the response of plasmin activity to PPACK and PPACK nanoparticles (FIG. 4). Greater than 80% inhibition of plasmin activity against Chromozym TH was achieved with 138 μM PPACK, both for free PPACK and particle-bound inhibitor. Conjugation of PPACK to nanoparticles constitutes an N-terminal modification to the inhibitor that does not compromise its specificity for thrombin over plasmin.

Example 3. Antithombotic Efficacy In Vivo

Figure 5:
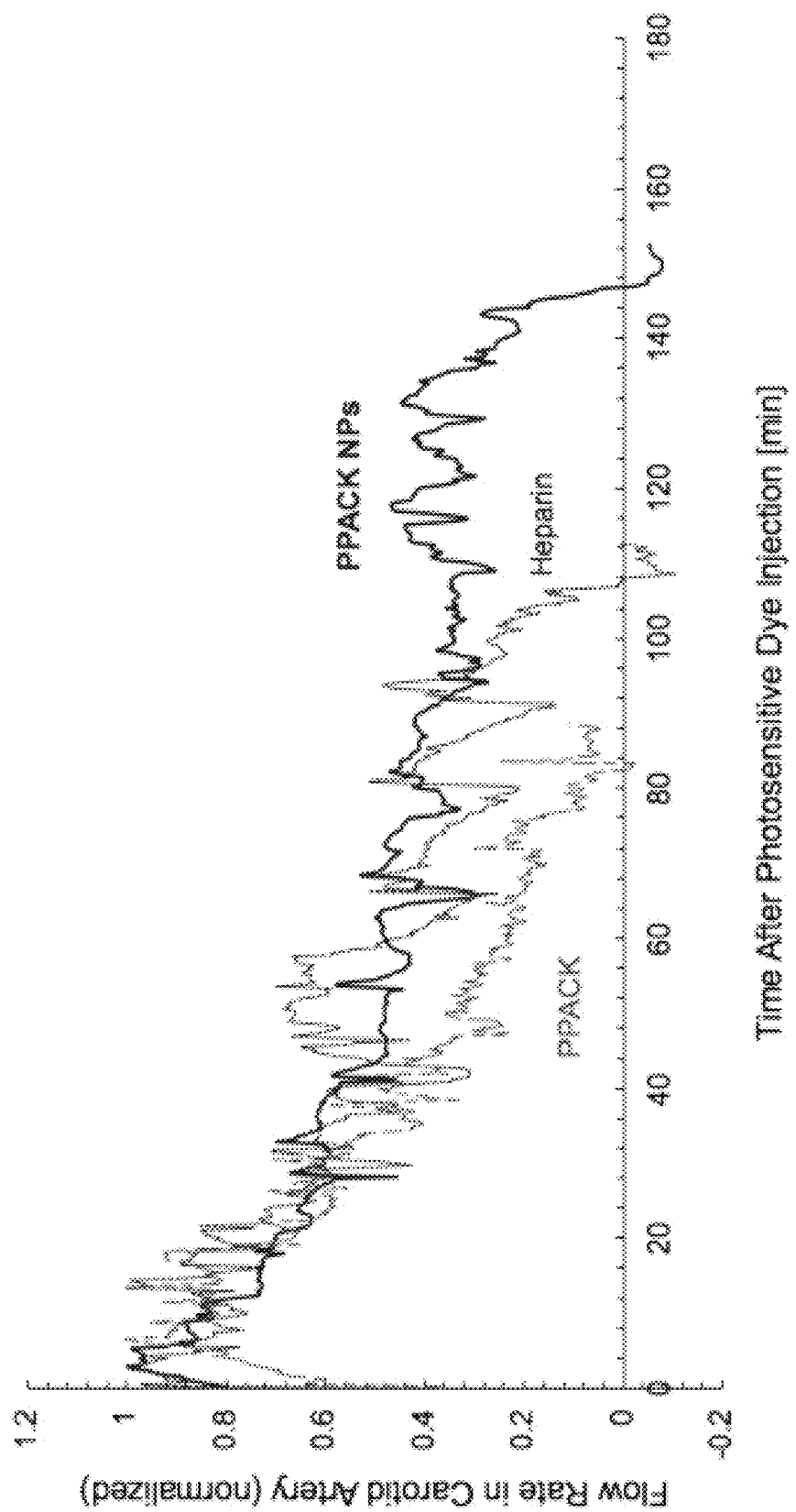
FIG. 5 depicts a graph. Photochemical injury was used to induce thrombotic occlusion of the mouse carotid artery while monitoring blood flow. Representative blood flow time courses for animals treated with PPACK (red), heparin (black), or PPACK-nanoparticles (blue) are depicted. In the presence of PPACK-nanoparticles or heparin, formation of a stable thrombus was noticeably delayed, whereas free PPACK allowed a steady approach to complete occlusion.
Figure 6A:
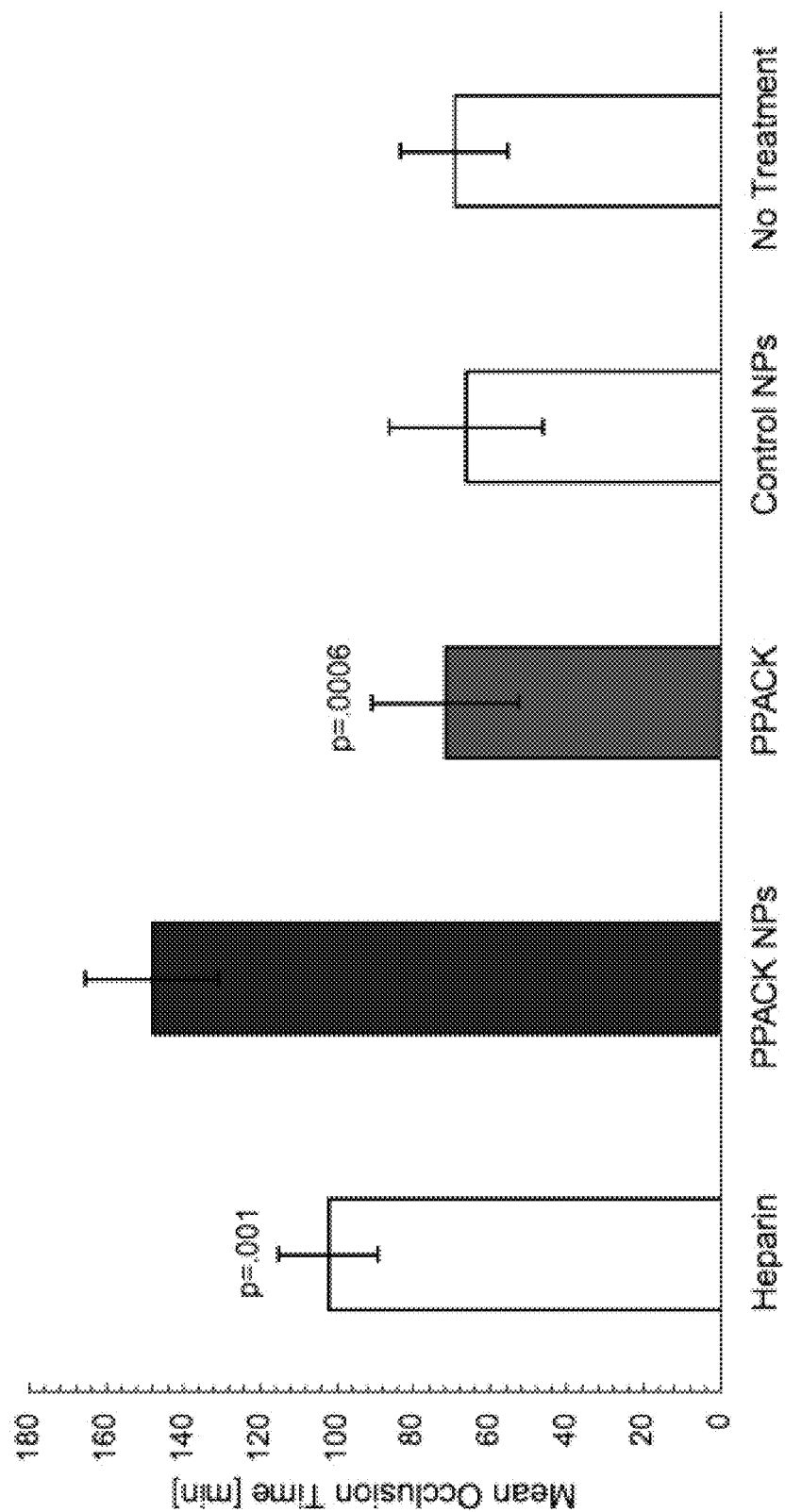
FIG. 6 depicts graphs illustrating mean±standard deviation occlusion time for each tested treatment condition in photochemical thrombotic injury experiments. Treatment with PPACK (n=7) or non-functionalized nanoparticles (n=7) did not delay occlusion time. PPACK-nanoparticle treatment more than doubled occlusion time over PPACK-treated (p=0.0006) or non-treated mice (n=7). PPACK-nanoparticle treatment also lengthened occlusion time relative to heparin treatment (p=0.001, n=4) (A). In blood draws, PPACK nanoparticles delayed the APTT only briefly, with systemic coagulation times approaching control values over the first 20 minutes after injection (B).

In trials of the in vivo effect of PPACK nanoparticles, thrombotic occlusion of the carotid artery was induced in C57BL/6 mice. Blood flow in the carotid steadily diminished as occlusion progressed (FIG. 5). Time to occlusion indicated efficacy of fibrin and platelet deposition. Saline, heparin, non-functionalized nanoparticles, PPACK, or PPACK nanoparticles were administered ten minutes before inducing laser injury via injection of rose bengal dye (FIG. 6A). With saline sham treatment, carotid artery occlusion occurred at 70±17 minutes after dye injection. Following a bolus of control nanoparticles, occlusion occurred at 66±14 minutes. PPACK alone, despite its efficacy as a thrombin inhibitor in vitro, also exerted no apparent impact on thrombus formation in vivo, resulting in a mean occlusion time of 71±19 minutes. The absence of an antithrombotic effect for PPACK accords with the expectation of a 2.9-minute reported clearance half-life and with the known in vivo instability of PPACK without protection of the N-terminus.

Heparin, however, has well-characterized antithrombotic effects and is a standard option as an anticoagulant for mediation of acute thrombus formation. Previous trials with the rose bengal thrombosis model yielded an occlusion time of 97±18 minutes for heparin at a dose of 0.125 mg/kg animal weight [31]. Here, occlusion occurred at 102±13 minutes (FIG. 6A).

Occlusion time more than doubled to 145±13 minutes in the mice treated with a 1 ml/kg dose of PPACK nanoemulsion (FIG. 6A). As compared to a high dose of heparin, PPACK nanoparticles outperformed (p<0.001) the established anticoagulant. Likewise, both PPACK nanoparticles (p<0.001) and heparin (p<0.05) extended time to occlusion of the carotid over PPACK treatment.

Figure 6B:
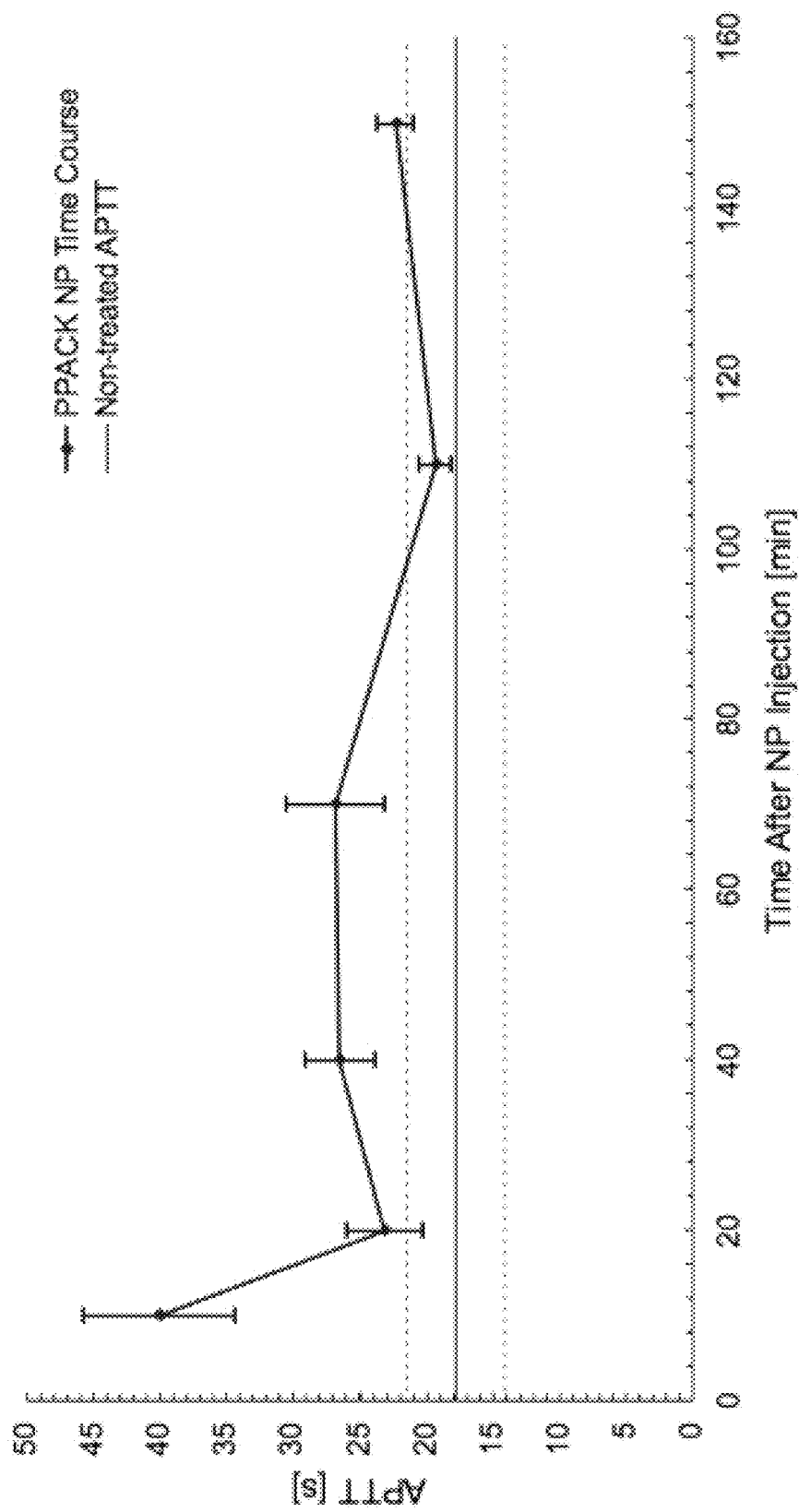
Figure 7:
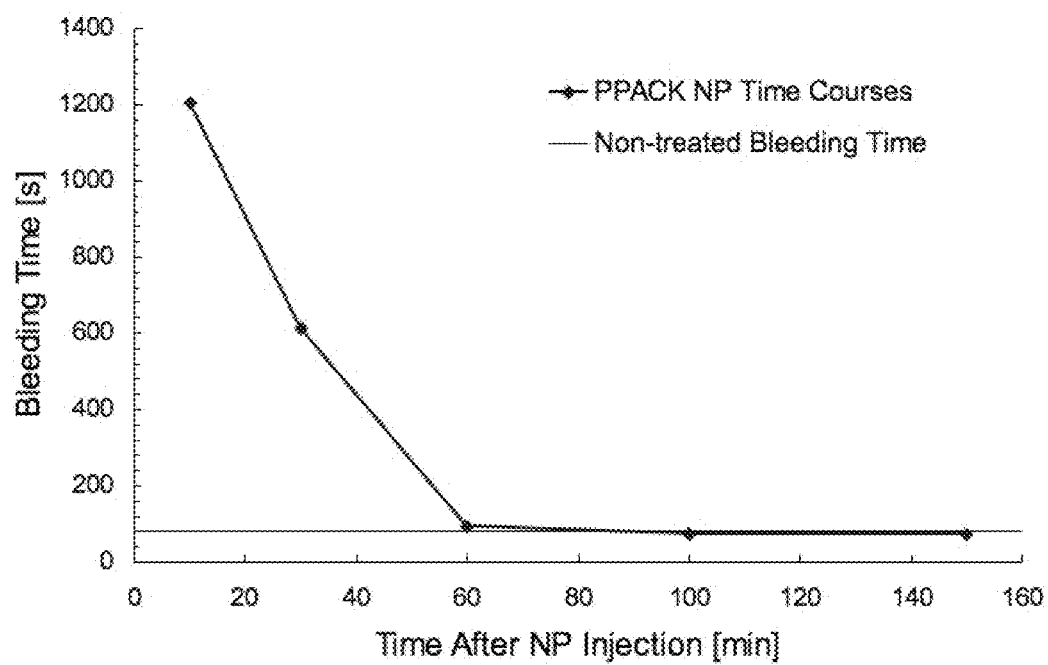
FIG. 7 depicts a graph. Bleeding times were measured via distal tail injury at selected times after tail vein bolus of PPACK nanoparticles at 1 ml/kg. All depicted data are for n=1.

Activated partial thromboplastin time (APTT) for treatment with control nanoparticles did not significantly differ from APTT for saline treatment. At 10 minutes after injection of PPACK nanoparticles, coagulation time was significantly lengthened. However, blood withdrawn at 20 minutes after injection nearly matched control APTT values. Subsequent blood draws yielded APTTs that did not significantly differ from control values (FIG. 6B), indicating fast abatement of the systemic effects of the PPACK particles despite prolonged therapeutic effect. A similar time course was evident in preliminary measurements of bleeding times in the tail after administration of PPACK nanoparticles as a tail vein bolus (FIG. 7).

Figure 8A:
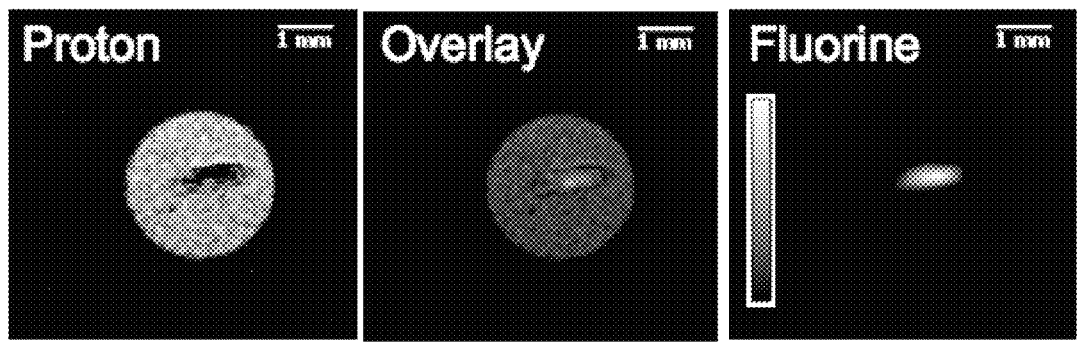
FIG. 8 depicts an excised occluded artery from a mouse treated with PPACK nanoparticles. In mice receiving treatment with control nanoparticles (n=3) or PPACK nanoparticles (n=3), both carotid arteries were excised following induction of occlusive thrombi in the right carotid artery. $^{19}$F MRI at 11.7 T exhibited coregistration of $^{19}$F signal from PPACK nanoparticles with $^1$H images depicting the occlusive clot in the artery (A). $^{19}$F MRS was used to quantify retention of nanoparticles in the injured right carotid artery (RA) and the unharmed left carotid artery (LA) for the two tested nanoparticle treatments. Retained particles±standard error are represented in (B).

$^{19}F$ magnetic resonance imaging and spectroscopy were used to assess Perfluoro 15-Crown-5 Ether (CE) NMR signal present in selected arteries due to retention of PFC nanoparticles. FIG. 8A depicts an excised occluded artery from a mouse treated with PPACK nanoparticles. In the left panel, a proton MRI illustrates a 0.2 mm cross-section of the artery with a dense clot in the center. A false color $^{19}F$ 1 mm projection image in the right panel depicts nanoparticle content in the artery. An overlay of the two images indicated strong colocalization of the particles with the clot, implying the possibility of tracking PPACK nanoparticles as they act to interrupt clot formation.

Figure 8B:
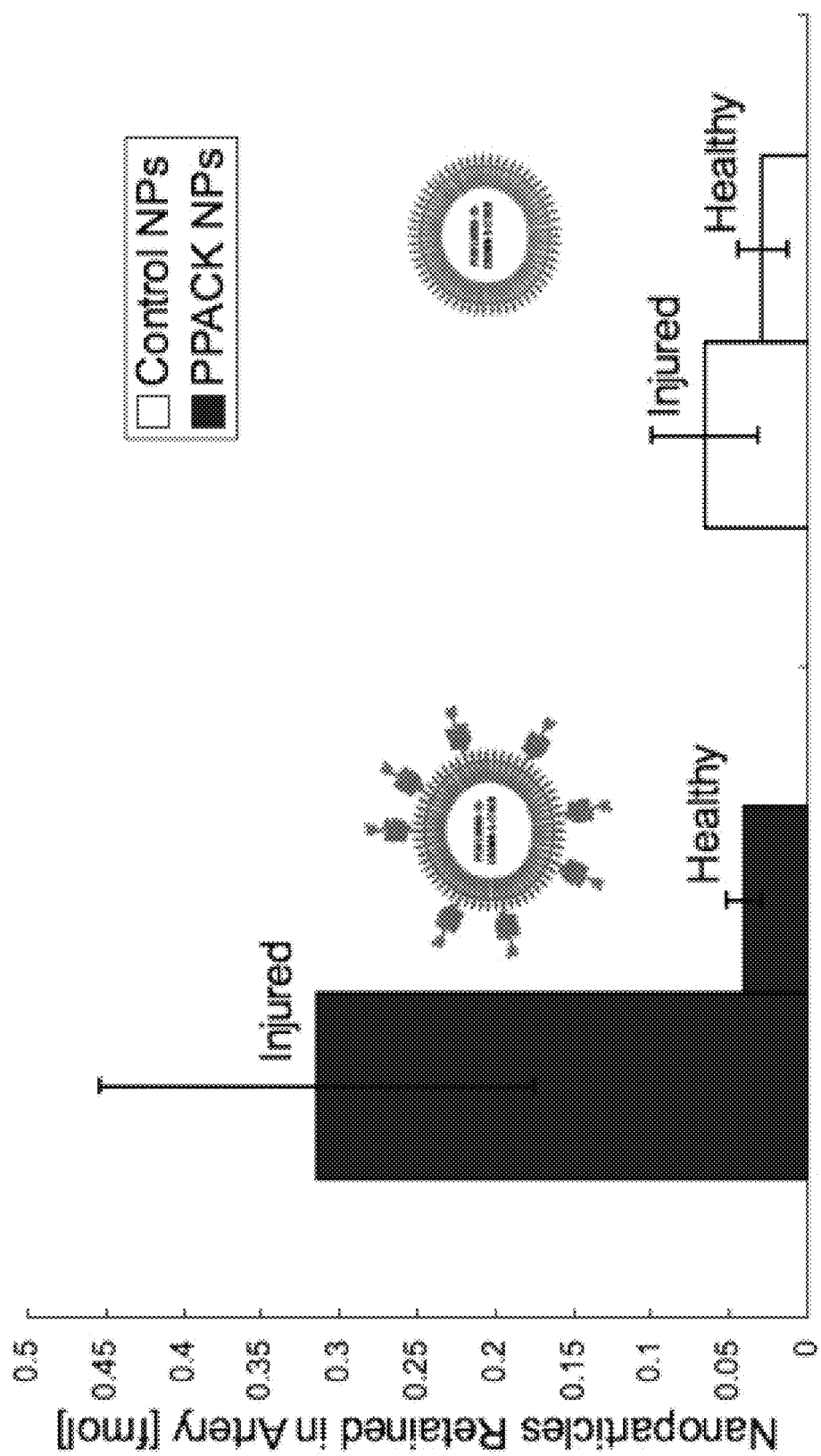

Quantitative $^{19}F$ spectroscopy was employed to quantify nanoparticle incorporation into clots from six mice (FIG. 8B). In mice treated with PPACK nanoparticles, injured arteries retained 0.31±0.14 fmol and unaffected arteries retained 0.04±0.01 fmol nanoparticles. In mice treated with control nanoparticles, injured arteries retained 0.07±0.03 fmol and uninjured arteries retained 0.03±0.02 fmol.

Figure 9:
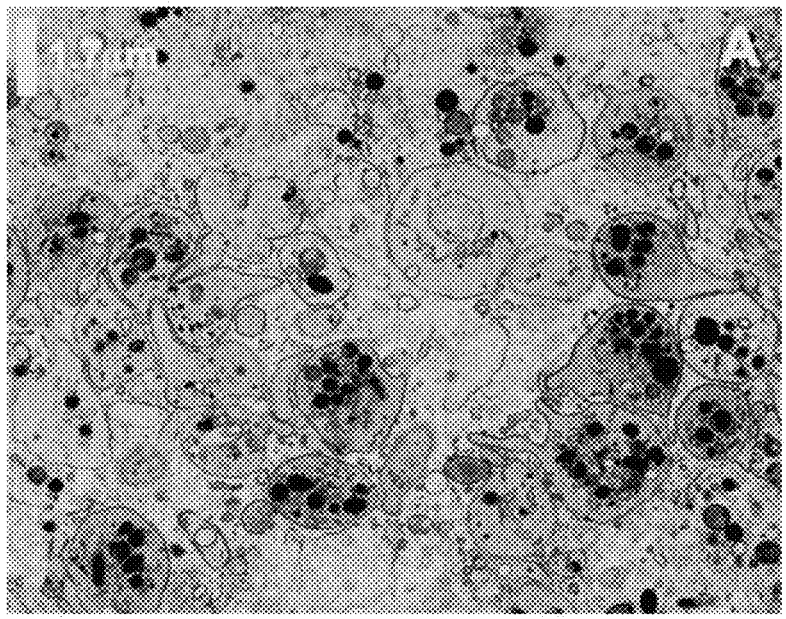
FIG. 9 depicts photomicrographs. TEM was used to characterize microstructure of excised clots formed during PPACK nanoparticle or control nanoparticle treatment. Clots formed in the presence of PPACK-nanoparticles had loosely associated platelets with little evidence of degranulation (A). Close association, degranulation, and interdigitation of platelets was evident in clots formed in the presence of control nanoparticles (B).
Figure 9:
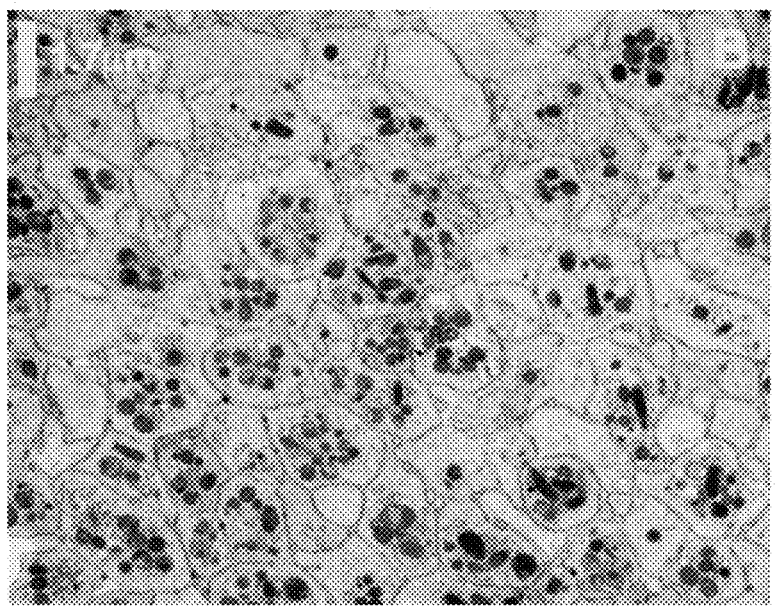

To further elucidate the mechanism by which PPACK nanoparticles prevent thrombus formation, TEM was used to examine the microstructure of fully formed thrombi. In clots formed after treatment with PPACK nanoparticles, few degranulated platelets were observed. Furthermore, platelets in such clots were loosely associated with one another, showing no signs of the dense packing evident in well-formed platelet aggregates. Instead, a fibrin gel appeared to dominate the clot microstructure (FIG. 9A). In TEM images of clots subject to control nanoparticle treatment, close association and interdigitation of platelets was evident. Similarly, degranulated platelets were abundant in these thrombi (FIG. 9B).

Figure 10:
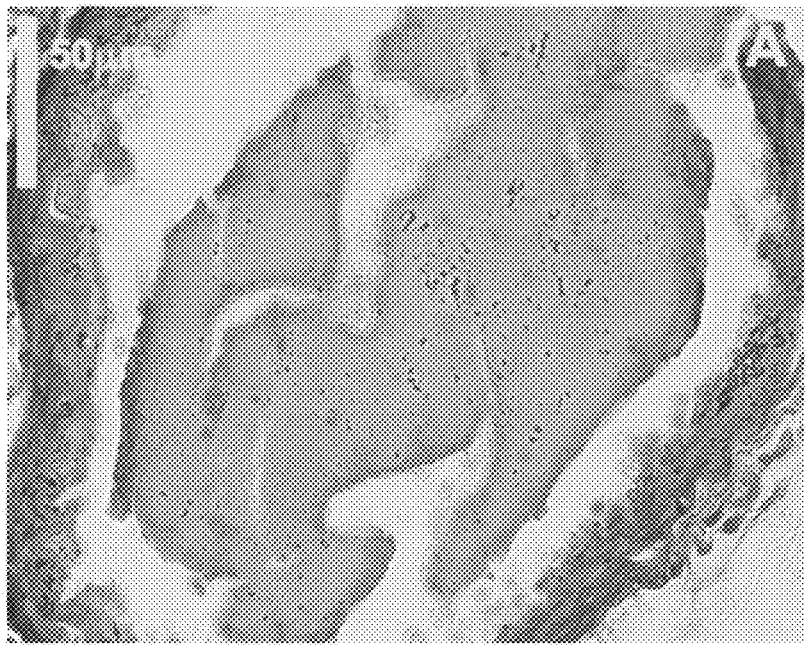
FIG. 10 depicts photomicrographs. Carstair's staining of clots subject to treatment with PPACK nanoparticles (A) or control nanoparticles (B) helped to examine the nature of the clots formed with each treatment. Clots formed in the presence of PPACK nanoparticles exhibited sparse staining of platelets (blue in the central region) and large amounts of isolated fibrin (pink in the central region) (A). With control nanoparticle treatment, staining of platelets was more prominent (B).
Figure 10:
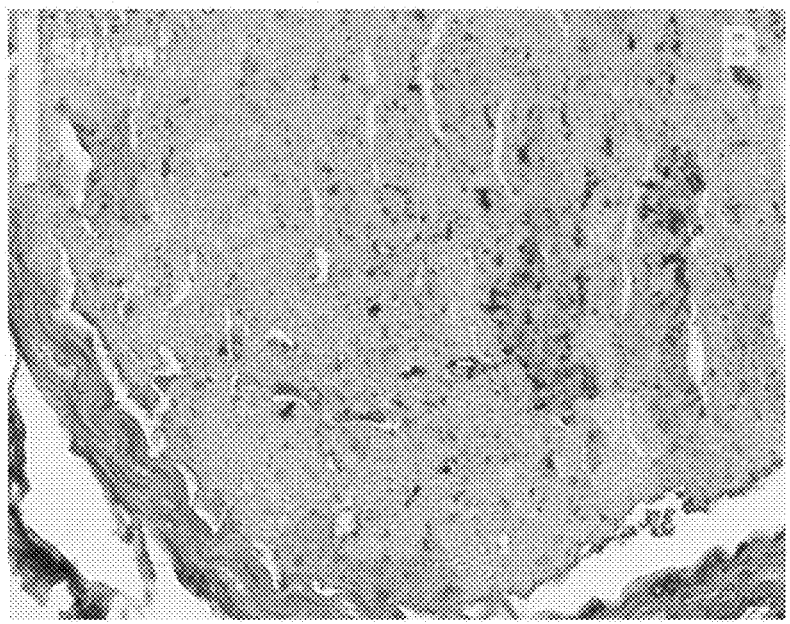
Figure 11:
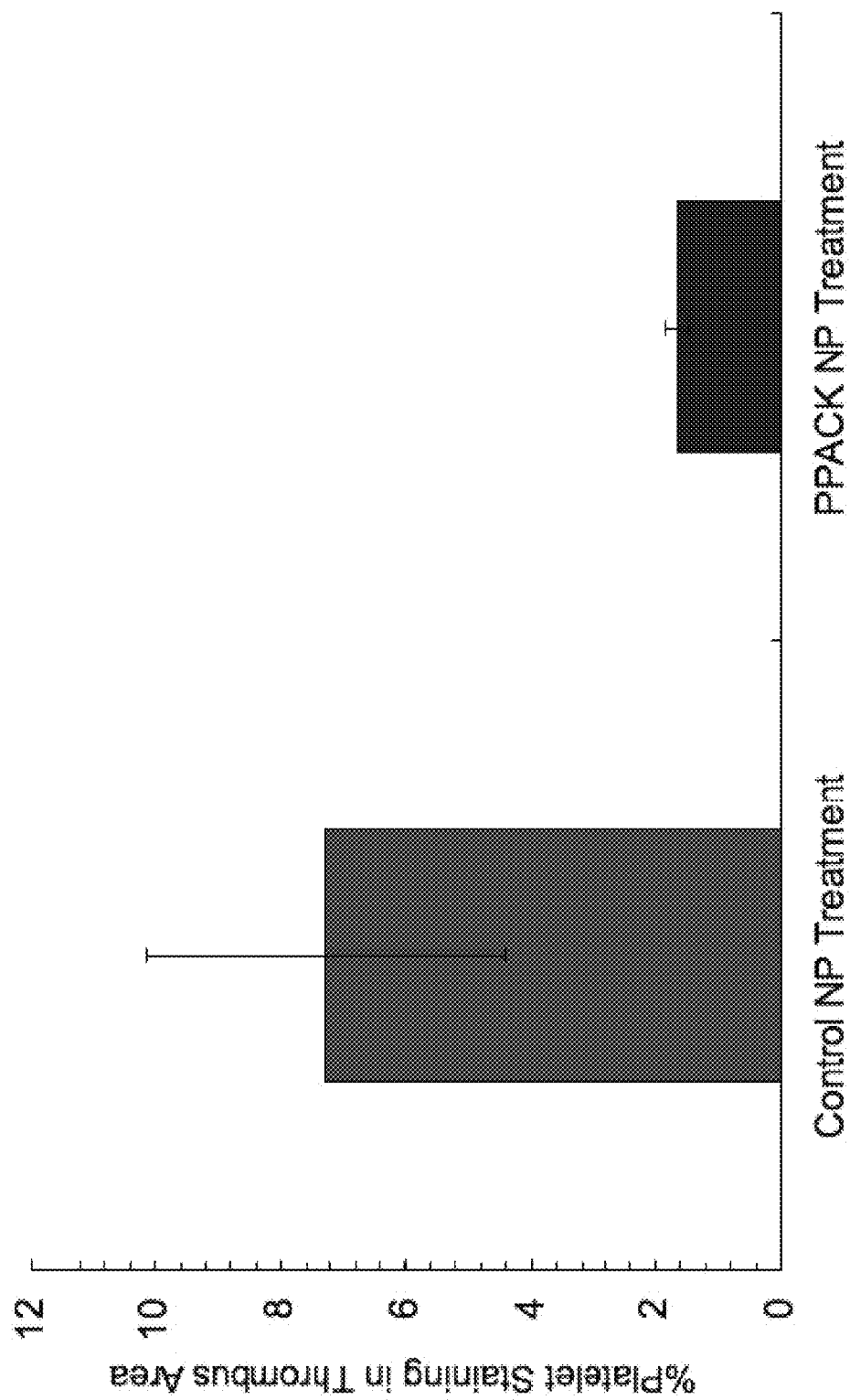
FIG. 11 depicts a plot. Area occupied by platelet staining within Carstair's stained thrombi was evaluated in NIH Image J. For three arteries treated with control nanoparticles, platelet staining occupied 7.28%±2.87% of thrombus area. For three arteries treated with PPACK nanoparticles, platelet staining occupied 1.66%±0.18% of thrombus area.

Carstair's staining was used to assess relative amounts of platelets and fibrin in selected clots. Staining of clots formed after PPACK nanoparticle treatment indicated a predominance of fibrin with only sparse clusters of platelets (FIG. 10). For clots formed in the presence of control nanoparticles, platelet staining was denser and interconnected (taking up 7.28% of clot area as opposed to 1.66% in PPACK-treated clots) (FIG. 11).

Discussion for Examples 1-3

The goal of the examples above was to design a therapeutically active nanoparticle with inherent targeting to proliferating thrombi. A PFC nanoparticle anticoagulant that features covalently bound PPACK as its active component was synthesized and implemented. Whereas PPACK itself is not clinically useful as an antithrombotic [2, 27], the examples demonstrate the PPACK nanoparticle to be an effective intravenous anticoagulant. The rose bengal thrombosis model was chosen for its demonstrated sensitivity to a wide range of anticoagulants. The time to arterial occlusion in this model has shown susceptibility to treatment with notable thrombin inhibitors [32]. The rose bengal model demonstrates that the PPACK nanoparticle may delay localized occlusive thrombosis while minimizing systemic effects on bleeding times.

Imaging contrast provided by the particle core indicated that the particle inherently confines to the site of thrombosis, explaining the highly targeted therapeutic effect. Given the colocalization of the particle to sites of thrombosis and the extensive previous use of PFC particles to provide magnetic resonance, ultrasound, optical and SPECT contrast [29, 33-35], PPACK nanoparticles have potential as a tool for diagnostic mapping of thrombosis. As shown previously for fibrin in clots [36, 37], $^{19}$F signatures from the PFC core may be quantified in molarity to provide a gross estimate of their local concentration, indicative of the binding at the site of thrombosis in this case.

The pharmacokinetics of functionalized PFC nanoparticles have been established in previous work exploring the use of such particles in drug delivery and imaging applications [28, 29]. Through these studies and in a long history of use in blood transfusions [28], the in vivo safety and stability of PFC emulsions has been established. Stable attachment of covalently bound targeting ligands has also been demonstrated [38-40]. Building on this work, the antithrombotic nanoparticle presents a direct thrombin inhibitor on its surface during circulation and upon retention at a site of developing thrombosis. The fundamentally different in vivo behavior of PPACK on the particle may be attributed to both prolonged circulation and sequestration at the site of thrombosis.

Analysis of thrombotic occlusions formed in the presence of PPACK particles indicates that, as part of its therapeutic impact, the antithrombotic particle impacts platelet deposition. The particle likely inhibits thrombin's ability to activate platelets via PAR cleavage [17-21]. As evaluated with Carstair's staining (FIG. 10) and with TEM (FIG. 9), the morphology of the clots formed after PPACK particle treatment is distinguished by sparse platelet distribution and reduced density of packing. Although thrombin inactivation is not the traditional route to antiplatelet therapy, antiplatelet activity is a useful effect of thrombin targeting. Thus, the apparent reduction in platelet deposition in the treatment evidences a possible broader clinical application for the particle as a combined antithrombotic and antiplatelet agent.

Anticoagulants that are mechanistically based on thrombin inhibition abound in standard clinical practice. Most notably, heparin binding dramatically accelerates the inhibition of thrombin by antithrombin and by heparin cofactor II [31]. However, deficiencies in antithrombin or heparin cofactor II are well documented [7, 41-43]. Further evidence indicates that the activity of antithrombin-heparin is significantly abated when the inhibitory complex is bound in a growing thrombus [44]. A preference for thrombin inhibition with direct, high-affinity, and specific inhibitors has evolved in recent years.

The design of specific and potent direct thrombin inhibitors has garnered attention from numerous researchers. However, problems of specificity, toxicity, and unacceptable circulating half-life have plagued many otherwise promising lead compounds [3, 45]. Amongst direct thrombin inhibitors, PPACK was used here as a reasonably cheap, small, and non-toxic [27] agent to complex with PFC nanoparticles. However, other known thrombin inhibitors could be employed. Flexible conjugation schemes abound, given that diphospholipids with large varieties of linking groups and spacers are readily available commercially. Different inhibitor concentrations could also be tested. The PFC nanoparticle thrombin inhibitor model would likely retain its noted advantages with adaptation to different inhibitory moieties.

Regardless of the drug that is conjugated to the particle, the antithrombotic nanoparticle is designed to act as a unique inhibitor in its own right. Rather than serving as a vehicle that delivers an antagonist to the thrombin target, the particle holds onto the inhibitor and acts against thrombus formation by maintaining localized thrombin-absorbing surfaces that are not disabled after locating a thrombin target.

In recent clinical trials, problems of toxicity (in the case of the reversible thrombin inhibitor Ximelagatran [45]) or ambiguous patient outcome (in the case of the P2Y12 inhibitor Ticragelor [46]) have raised questions of efficacy and labeling in otherwise promising anticoagulants used in acute coronary syndromes. There continues to be a need for new potent and highly specific antithrombotic agents with minimal toxicity for the treatment of thrombosis in acute coronary syndromes [10-12], stroke [13], venous thrombosis [11, 14], and stent placement [47, 48]. The particle developed here may be used in acute treatments, as a potent, more effective local therapy with an improved safety profile that serves as a bridge to outpatient oral therapy.

Example 4. Nanoparticles Functionalized with Bivalirudin

Figure 12:
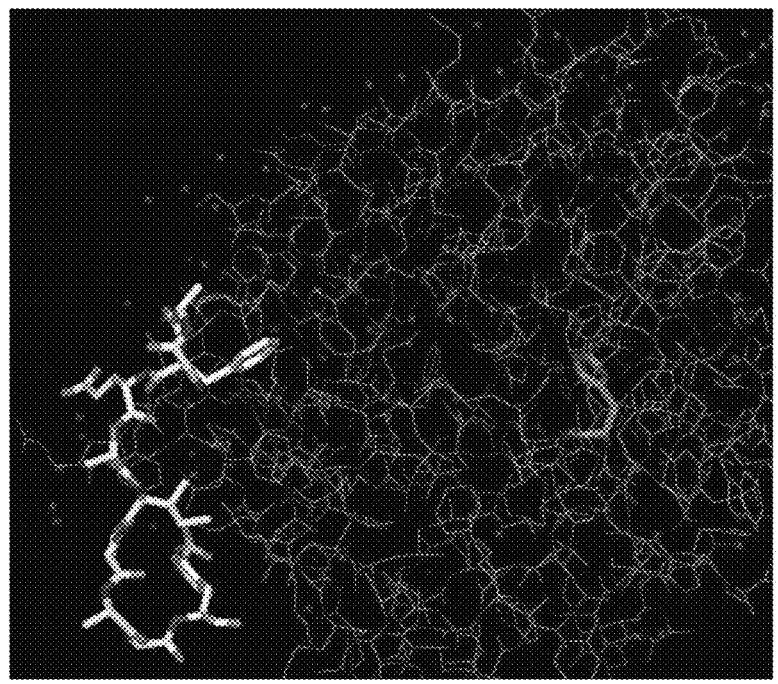
FIG. 12 depicts molecular models of Bivalirudin inhibition sites on thrombin.
Figure 12:
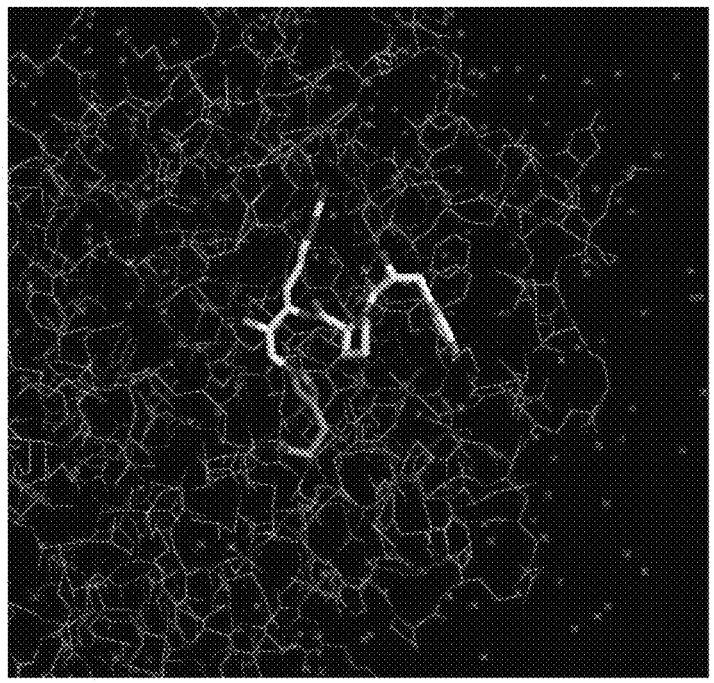

Bivalirudin (Hirulog) is a specific and reversible direct thrombin inhibitor (DTI). Bivalirudin inhibits thrombin by specifically binding both to the anion-binding exosite I (FIG. 12A) and to the active site (FIG. 12B) of circulating and clot-bound thrombin. Bivalirudin overcomes many limitations seen with indirect thrombin inhibitors, such as heparin. Bivalirudin is a short, synthetic peptide that inhibits both circulating and clot-bound thrombin, while also inhibiting thrombin-mediated platelet activation and aggregation. Bivalirudin has a quick onset of action and a short half-life. It does not bind to plasma proteins (other than thrombin) or to red blood cells. Therefore it has a predictable antithrombotic response. There is no risk for Heparin Induced Thrombocytopenia/Heparin Induced Thrombosis-Thrombocytopenia Syndrome (HIT/HITTS), it does not require a binding cofactor such as antithrombin and does not activate platelets. These characteristics make Bivalirudin an ideal alternative to heparin.

Figure 13A:
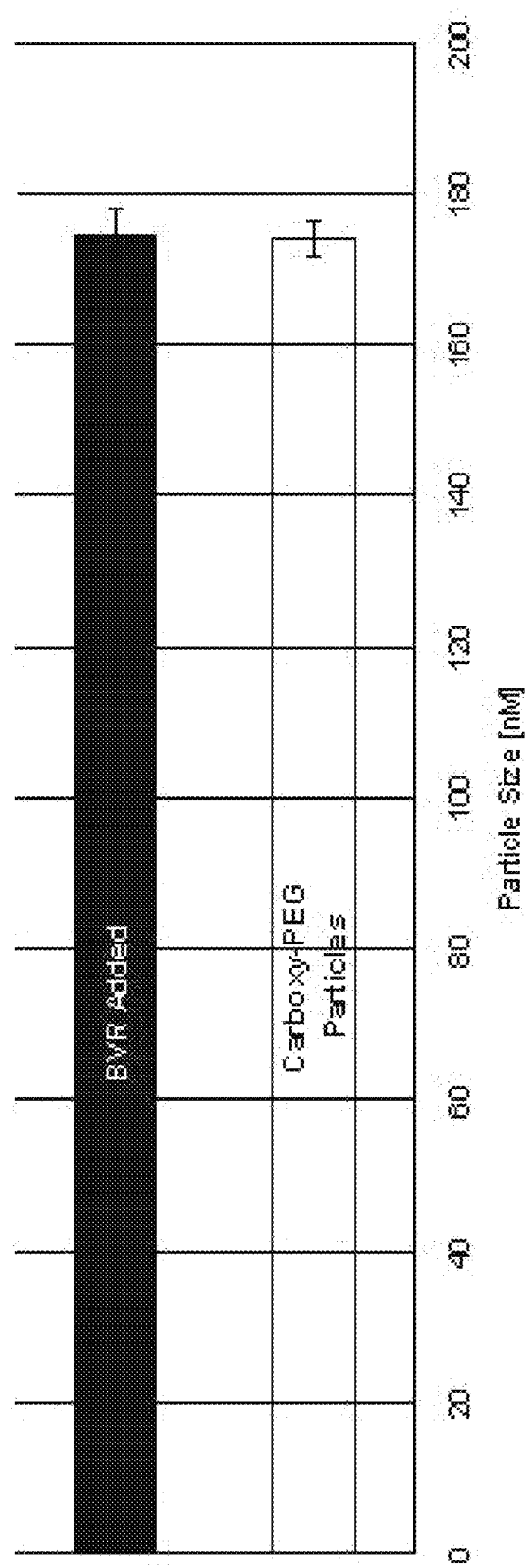
FIG. 13 depicts two plots. Particle size was measured before and after addition of Bivalirudin to nanoparticles. The addition of Bivalirudin did not significantly change the mean hydrodynamic particle diameter (top panel). Corresponding to conjugation of Bivalirudin to carboxy-terminated lipids, the particle zeta potential after functionalization.
Figure 13B:
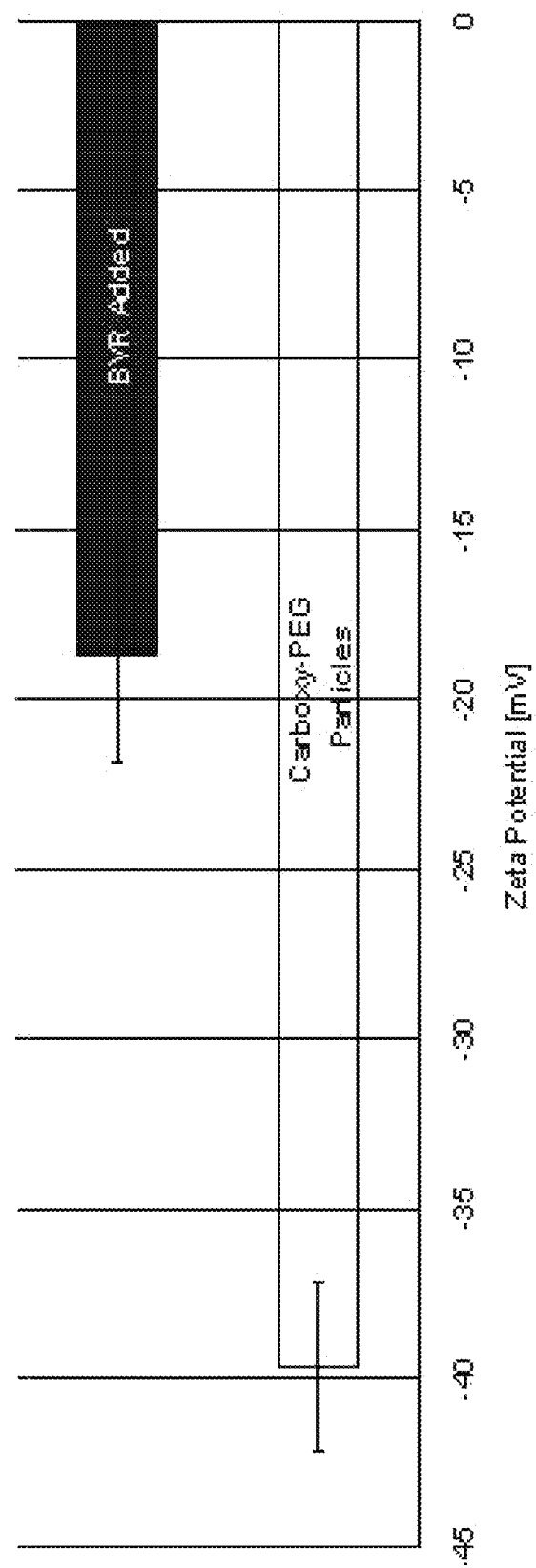

Bivalirudin was conjugated to Carboxy-PEG functionalized nanoparticles at the N-terminus using procedure described in the Materials and Methods for Examples 1-3 above. After conjugation of Bivalirudin, nanoparticles were examined to verify stability, and found to have analogous coupling and stability characteristics (FIGS. 13A and B) to the PPACK particles described in Examples 1-3.

Figure 14:
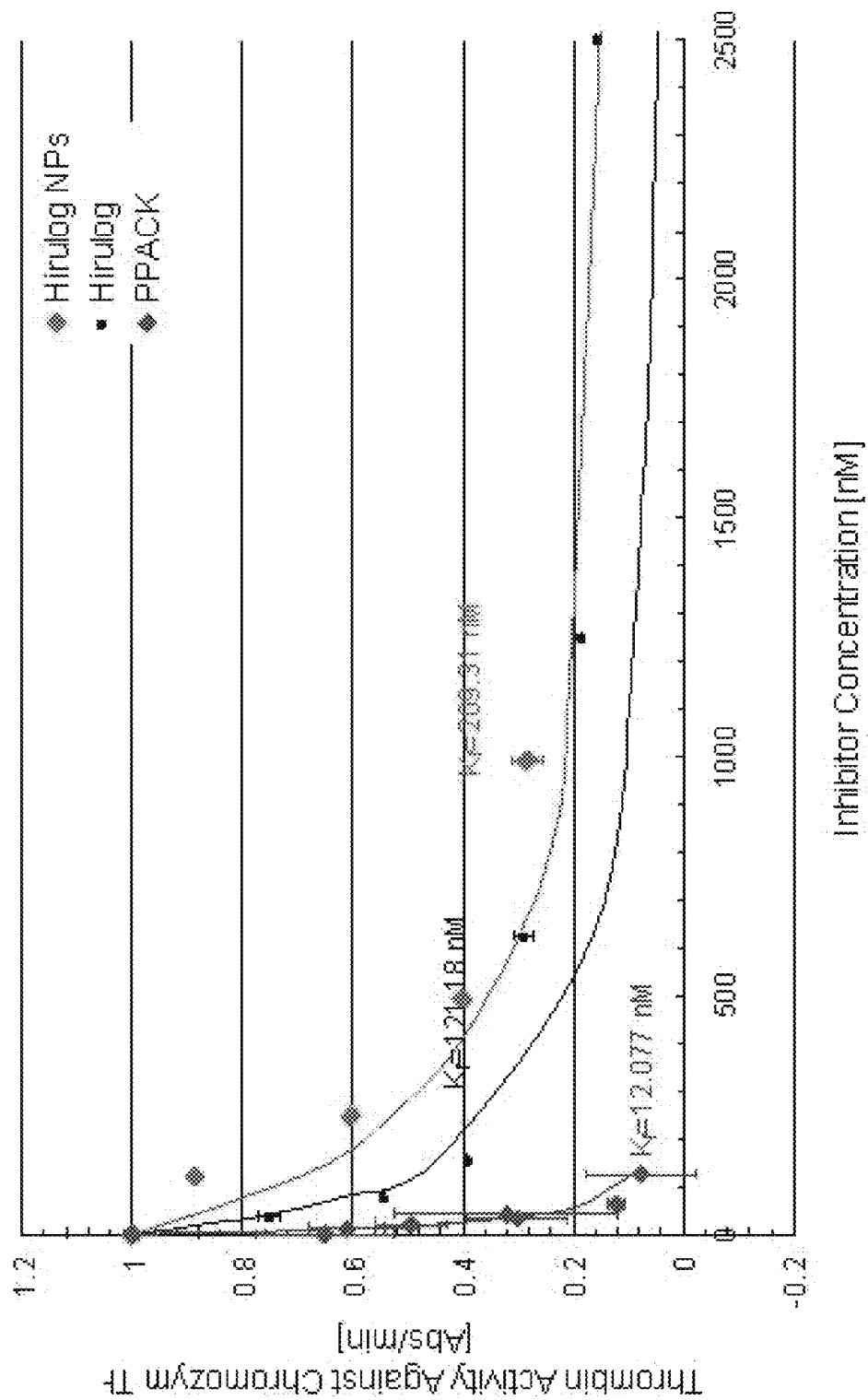
FIG. 14 depicts a graph illustrating the activity of the antithrombotic nanoparticle.

Bivalirudin and Bivalirudin nanoparticle inhibition of thrombin was evaluated and compared to inhibition of thrombin by PPACK (FIG. 14). The results show that Bivalirudin is less active, but more specific than PPACK. In addition, Bivalirudin activity, as with PPACK, was not significantly diminished on the particles.

Figure 15:
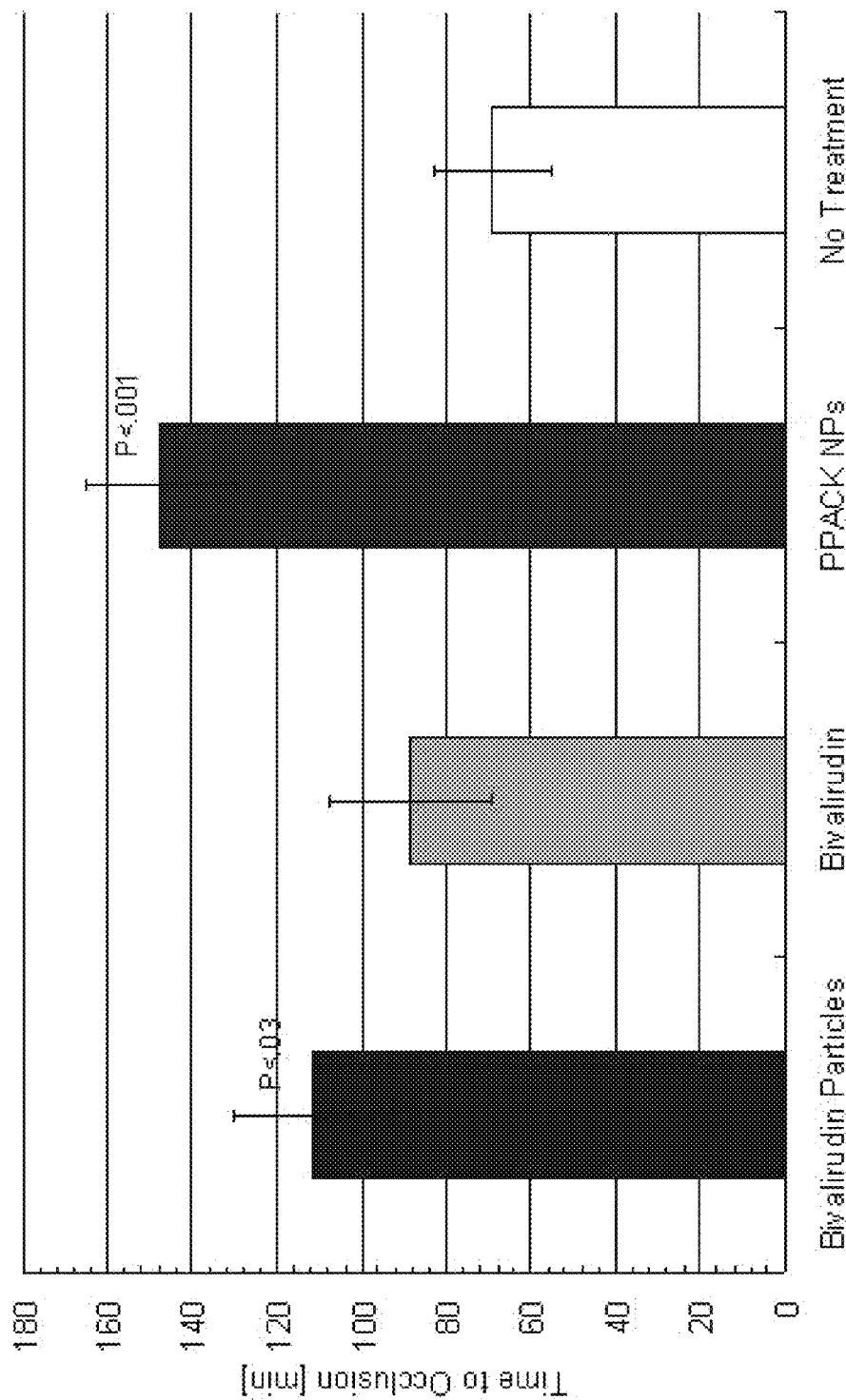
FIG. 15 depicts a graph illustrating mean±standard deviation occlusion time for each tested treatment condition in photochemical thrombotic injury experiments.

The in vivo effect of Bivalirudin nanoparticles was measured as described in Examples 1-3 above, and compared to PPACK nanoparticles (FIG. 15). At the administered dose, Bivalirudin did not significantly extend occlusion time, but Bivalirudin nanoparticles did. PPACK nanoparticles on the other hand, outperformed both Bivalirudin treatments when using an identical dose. Even though Bivalirudin has been shown to provide more effective action against fibrin-bound thrombin (activity against exosite I), Bivalirudin particles may be more likely to release from the target due to cleavage of the inhibitor by thrombin.

Figure 16:
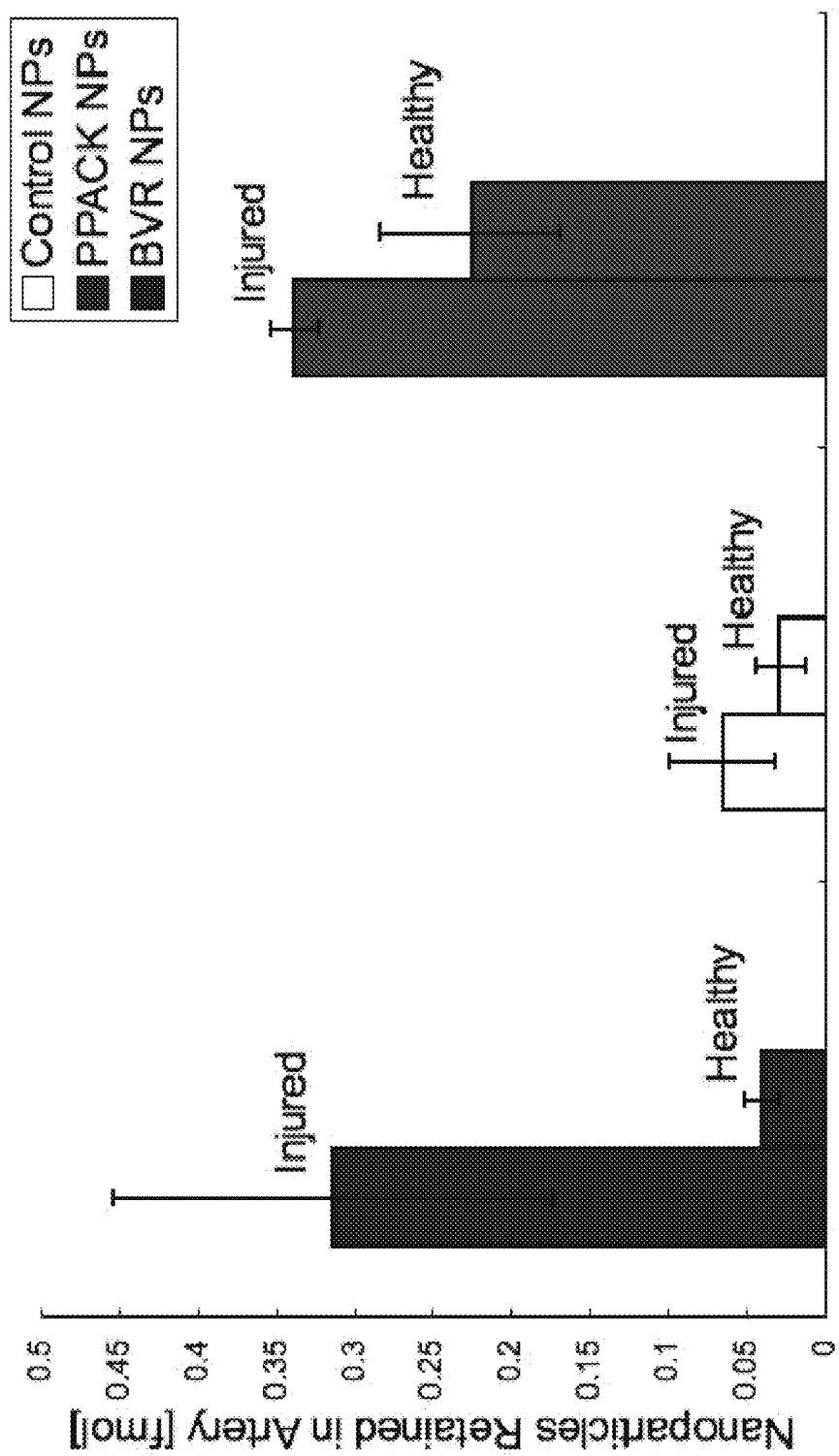
FIG. 16 depicts a graph illustrating the amount of nanoparticles retained in an artery. $^{19}$F MRS was used to quantify retention of nanoparticles in the injured right carotid artery (RA) and the unharmed left carotid artery (LA) for the three tested nanoparticle treatments. Retained particles±standard error are represented in the graph.

$^{19}$F magnetic resonance imaging and spectroscopy were used to assess Perfluoro 15-Crown-5 Ether (CE) NMR signal present in selected arteries due to retention of PFC nanoparticles (FIG. 16).

Human fibrin clots were formed via activation of citrated plasma with thrombin and 500 mM CaCl$_2$ as described previously (Morawski A M et al (2004) 52: 1255-1262.). For thrombin-targeted particles, clots were incubated with 1:15 dilution of emulsion at 37 degrees for two hours on a rotating platform shaker prior to rinsing and quantitative $^{19}$F spectroscopy. For fibrin targeting, clots were incubated with 125 ug of biotinylated 1H10 antibody at 4 degrees for 12 hours prior to incubation with avidin-functionalized nanoparticles at 37 degrees as with thrombin targeting (FIG. 17).

REFERENCES

1. Davies M J (1992) Anatomic features in victims of sudden coronary death. Coronary artery pathology. Circulation 85: 119-124.
2. Kaiser B, Hauptmann J (1992) Pharmacology of Synthetic Thrombin inhibitors of the tripeptide type. Cardiovascular Drug Reviews 10: 71-87.
3. Srivastava S, Goswami L N, Dikshit D K (2005) Progress in the design of low molecular weight thrombin inhibitors. Medicinal Research Reviews 25: 66-92.
4. Di Cera E (2008) Thrombin. Molecular Aspects of Medicine 29: 203-254.
5. Furie B, Furie B C (2008) Mechanisms of thrombus formation. The New England Journal of Medicine 359: 938-949.
6. Tait R C, Maclean P C (2007) Hereditary and acquired antithrombin deficiency epidemiology, pathogenesis and treatment options. Drugs 67: 1429.
7. Tran T H, Marbet G A, Duckert F (1985) Association of hereditary heparin cofactor II deficiency with thrombosis. Lancet 2; 413-414.
8. Ansell J, et al. (2004) The pharmacology and management of the vitamin K antagonists. Chest 126: 204S-233S.
9. Schwartz R S, et al. (2009) Microemboli and microvascular obstruction in acute coronary thrombosis and sudden coronary death: relation to epicardial plaque histopathology. Journal of the American College of Cardiology 54(23): 2167-2173.
10. Lee L V (2008) Anticoagulants in coronary artery disease. Clinical Cardiology 26: 615-628.
11. Turpie A G (2008) The top four advances in antithrombotic care in the last year. Thrombosis Research 123: S2-S6.
12. Fareed J, et al. (2008) Changing trends in anti-coagulant therapies. Are heparins and oral anti-coagulants challenged? International Journal of Angiology 27: 176-192.
13. Bousser M G (2009) Antithrombotic agents in the prevention of ischemic stroke. Cerebrovascular Diseases 27: 12-19.
14. Gross P, Weitz J I (2009) New antithrombotic drugs. Clinical Pharmacology and Therapeutics 86: 139-146.
15. Bode W, et al. (1989) The refined 1.9 Å crystal structure of human a-thrombin: interaction with D-Phe-Pro-Arg chloromethylketone and significance of the Tyr-Pro-Pro-Trp insertion segment. The EMBO Journal 8: 3467-3475.
16. Bode W, Turk D, Karshikov A (1992) The refined 1.9-Å crystal structure of D-Phe-Pro-Arg chloromethylketone-inhibited human alpha-thrombin: Structure analysis, overall structure, electrostatic properties, detailed active-site geometry, and structure-function relationships. Protein Science 1: 426-471.
17. Ivey M E, Little P J (2008) Thrombin regulates vascular smooth muscle cell proteoglycan synthesis via PAR-1 and multiple downstream signaling pathways. Thrombosis Research 123: 288-297.
18. Hirano K (2007) The roles of proteinase-activated receptors in the vascular physiology and pathophysiology. Arteriosclerosis, Thrombosis, and Vascular Biology 27: 27-36.
19. Coughlin S R (2000) Thrombin signaling and protease-activated receptors. Nature 407: 258-264.
20. Bretschneider E, et al. (2001) Evidence for functionally active protease-activated receptor-4 (PAR-4) in human vascular smooth muscle cells. British Journal of Pharmacology 132: 1441-1446.
21. Bretschneider E, et al. (2003) Evidence for functionally active protease-activated receptor-3 (PAR-3) in human vascular smooth muscle cells. Journal of Thrombosis and Haemostasis 90: 704-709.
22. Davie E W, Kulman J D (2006) Semin Thromb Hemostasis 32(Suppl 1):3-15.
23. Ghigliotti G, Waissbluth A R, Speidel C, Abendschein D R, Eisenberg P R (1998) Prolonged activation of prothrombin on the vascular wall after arterial injury. Arterioscler Thromb Vasc Biol 18:250-257.
24. Duguid J B (1946) Thrombosis as a factor in the pathogenesis of coronary atheroscle-rosis. J Pathol Bacterial 58:207-212.
25. Duguid J B (1948) Thrombosis as a factor in the pathogenesis of aortic atherosclerosis. J Pathol Bacteriol 60:57-61.
26. Kettner C, Shaw E (1979) D-Phe-Pro-ArgCH2Cl-A selective affinity label for thrombin. Thrombosis Research 14: 969-973.
27. Collen D, Matsuo O, Stassen J M, Kettner C, Shaw E (1982) In vivo studies of a synthetic inhibitor of thrombin. Journal of Laboratory and Clinical Medicine 99: 76-83.
28. Flaim S F. Pharmacokinetics and side effects of perfluorocarbon-based blood substitutes (1994) Artificial Cells, Blood Substitutes, and Immobilization Biotechnology 22: 1043-1054.
29. Hu G, et al. (2007) Imaging of vx-2 rabbit tumors with αvβ3-integrin-targeted 111 ln nanoparticles. International Journal of Cancer 120: 1951-1957.
30. Peters D, et al. (2009) Targeting atherosclerosis by using modular, multifunctional micelles. Proceedings of the National Academy of Sciences 106: 9815-9819.
31. Vicente C P, He L, Pavao M S G, Tollefsen D M (2004) Antithrombotic activity of dermatan sulfate in heparin cofactor II-deficient mice. Blood 104: 3965-3970.
32. Westrick R J, Winn M E, Eitzman D T (2007) Murine Models of Vascular Thrombosis. Arteriosclerosis, Thrombosis, and Vascular Biology 27: 2079-2093.
33. Winter P M, Caruthers S D, Wickline S A, Lanza G M (2006) Molecular imaging by MRI. Current Cardiology Reports 8: 65-69.
34. Partlow K C, et al. (2007) 19F magnetic resonance imaging for stem/progenitor cell tracking with multiple unique perfluorocarbon nanobeacons. The FASEB Journal 21: 1647-1654.
35. Marsh J N, et al. (2007) Molecular imaging with targeted perfluorocarbon nanoparticles: quantification of the concentration dependence of contrast enhancement for binding to sparse cellular epitopes. Ultrasound in Medicine and Biology 33: 950-958.
36. Flacke S, et al. (2001) Novel MRI contrast agent for molecular imaging of fibrin: Implications for detecting vulnerable plaques. Circulation 104: 1280-1285.
37. Morawski A M, et al. (2004) Quantitative "magnetic resonance immunohistochemistry" with ligand-targeted F-19 nanoparticles. Magnetic Resonance in Medicine 52: 1255-1262.
38. Lanza G M, et al. (2000) Molecular Imaging of Stretch-Induced Tissue Factor Expression in Carotid Arteries with Intravascular Ultrasound. Investigative Radiology 35(4): 227-234.
39. Winter P M, et al. (2003) Molecular Imaging of Angiogenesis in Nascent Vx-2 Rabbit Tumors Using a Novel $\alpha_v\beta_3$ targeted Nanoparticle and 1.5 Tesla Magnetic Resonance Imaging. Cancer Research 63: 5838-5843.
40. Winter P M, et al. (2003) Molecular Imaging of Angiogenesis in Early-Stage Atherosclerosis with $\alpha_v\beta_3$ Integrin-Targeted Nanoparticles. Circulation 108: 2270-2274.
41. Sie P, Dupouy D, Pichon J, Boneu B (1985) Constitutional heparin cofactor II deficiency associated with recurrent thrombosis. Lancet 2: 414-416.
42. Andersson T R, Larsen M L, Handeland G F, Abildgaard U. Heparin cofactor II activity in plasma: application of an automated assay method to the study of a normal adult population (1986) Scandinavian Journal of Haematology 36: 96-103.
43. Bertina R M, van der Linden I K, Muller H P, Brommer E J P (1987) Hereditary heparin cofactor II deficiency and the risk of development of thrombosis. Journal of Thrombosis and Haemostasis 57: 196-200.
44. Weitz J L, Hudoba M, Massel D, Maraganore J, Hirsh J (1990) Clot-bound thrombin is protected from inhibition by heparin-anti-thrombin III but is susceptible to inactivation by anti-thrombin III independent inhibitors. Journal of Clinical Investigation 86: 962-968.
45. Hirsh J, O'Donnell M, Eikelboom J W (2007) Beyond unfractionated heparin and warfarin. Circulation 116: 552-560.
46. Wallentin, L, et al. (2009) Ticagrelor versus Clopidogrel in Patients with Acute Coronary Syndromes. The New England Journal of Medicine 361: 1045-1057.
47. Kukreja N, Onuma Y, Daemen J, Serruys P W (2008) The future of drug-eluting stents. Pharmacological Research 57: 171-180.
48. May A E, Geisler T, Gawaz M (2008) Individualized antithrombotic therapy in high risk patients after coronary stenting. A double-edged sword between thrombosis and bleeding. Journal of Thrombosis and Haemostasis 99: 487-493.

What is claimed is:

1. An antithrombotic nanoparticle comprising a core and an outer layer, wherein the core comprises a perfluorocarbon that is a liquid at about 37° C. and the outer layer comprises a mixture of a lipid and a surfactant; and wherein the exterior of the nanoparticle comprises a direct thrombin inhibitor covalently conjugated to the exterior via the lipid component of the nanoparticle's outer layer, such that the nanoparticle has a second order kinetic constant for the direct thrombin inhibitor-thrombin interaction that is greater than the same kinetic constant of the direct thrombin inhibitor by itself, and wherein the nanoparticle is antithrombotic but does not substantially alter the clotting time of a subject's blood plasma.

2. The antithrombotic nanoparticle of claim 1, wherein the nanoparticle further comprises an anti-platelet agent.

3. The antithrombotic nanoparticle of claim 1, wherein the direct thrombin inhibitor is bivalirudin.

4. The antithrombotic nanoparticle of claim 1, wherein the direct thrombin inhibitor is D-phenylalyl-L-prolyl-L-arginyl-chloromethyl ketone (PPACK).

5. A composition, the composition comprising:
   a. a plurality of platelets,
   b. fibrin, and
   c. at least one nanoparticle comprising a core and an outer layer, wherein the core comprises a perfluorocarbon that is a liquid at about 37° C. and the outer layer comprises a mixture of a lipid and a surfactant; and wherein the exterior of the nanoparticle comprises a direct thrombin inhibitor covalently conjugated to the exterior via the lipid component of the nanoparticle's outer layer, such that the nanoparticle has a second order kinetic constant for the direct thrombin inhibitor-thrombin interaction that is greater than the same kinetic constant of the direct thrombin inhibitor by itself, and wherein the nanoparticle is antithrombotic but does not substantially alter the clotting time of a subject's blood plasma.

6. A method of decreasing, preventing, or imaging thrombus formation in a subject, the method comprising administering to the subject a nanoparticle comprising a core and an outer layer, wherein the core comprises a perfluorocarbon that is a liquid at about 37° C. and the outer layer comprises mixture of a lipid and a surfactant; and wherein the exterior of the nanoparticle comprises a direct thrombin inhibitor covalently conjugated to the exterior via the lipid component of the nanoparticle's outer layer, such that the nanoparticle has a second order kinetic constant for the direct thrombin inhibitor-thrombin interaction that is greater than the same kinetic constant of the direct thrombin inhibitor by itself, and wherein the nanoparticle is antithrombotic but does not substantially alter the clotting time of a subject's blood plasma.

7. The method of claim 6, wherein the nanoparticle further comprises an anti-platelet agent.

8. The method of claim 6, wherein the direct thrombin inhibitor is bivalirudin.

9. The method of claim 6, wherein the direct thrombin inhibitor is D-phenylalyl-L-prolyl-L-arginyl-chloromethyl ketone (PPACK).

10. The nanoparticle of claim 1, wherein the direct thrombin inhibitor is conjugated to the lipid component of the nanoparticle's coat via a linking molecule.

11. The nanoparticle of claim 1, wherein the direct thrombin inhibitor is directly conjugated to the lipid component of the nanoparticle's coat.

12. The method of claim 6, wherein the direct thrombin inhibitor is conjugated to the lipid component of the nanoparticle's coat via a linking molecule.

13. The method of claim 6, wherein the direct thrombin inhibitor is directly conjugated to the lipid component of the nanoparticle's coat.

* * * * *